US011177037B2

(12) United States Patent
Sanders et al.

(10) Patent No.: US 11,177,037 B2
(45) Date of Patent: *Nov. 16, 2021

(54) ADAPTIVE ATHLETIC ACTIVITY PRESCRIPTION SYSTEMS

(71) Applicant: NIKE, Inc., Beaverton, OR (US)

(72) Inventors: Daniel Sanders, Portland, OR (US); Brett S. Kirby, Portland, OR (US); David Clark, Beaverton, OR (US); Clifton W. Bynum, Portland, OR (US); Bradley W. Wilkins, Beaverton, OR (US); Philip F. Skiba, Highland Park, IL (US)

(73) Assignee: NIKE, Inc., Beaverton, OR (US)

( * ) Notice: Subject to any disclaimer, the term of this patent is extended or adjusted under 35 U.S.C. 154(b) by 42 days.

This patent is subject to a terminal disclaimer.

(21) Appl. No.: 15/459,626

(22) Filed: Mar. 15, 2017

(65) Prior Publication Data

US 2017/0266498 A1 Sep. 21, 2017

Related U.S. Application Data

(60) Provisional application No. 62/368,559, filed on Jul. 29, 2016, provisional application No. 62/353,394, (Continued)

(51) Int. Cl.
*A63B 24/00* (2006.01)
*G16H 40/67* (2018.01)
(Continued)

(52) U.S. Cl.
CPC ............. *G16H 40/67* (2018.01); *A41D 1/002* (2013.01); *A43B 3/0005* (2013.01); *A43B 5/00* (2013.01);
(Continued)

(58) Field of Classification Search
CPC ............. G09B 19/003; G09B 19/0038; G09B 19/0092; A63B 24/00; A63B 24/0075;
(Continued)

(56) References Cited

U.S. PATENT DOCUMENTS 8,533,001 B2   9/2013   Skiba
8,784,115 B1   7/2014   Chuang
(Continued)

FOREIGN PATENT DOCUMENTS

CN   101485563 A   7/2009
CN   102015037 A   4/2011
(Continued)

OTHER PUBLICATIONS

Jul. 4, 2017 - (WO) Isr & WO - App. No. PCT/US17/022556 (225127.02635).
(Continued)

*Primary Examiner* — Malina D. Blaise
(74) *Attorney, Agent, or Firm* — Banner & Witcoff, Ltd.

(57) ABSTRACT

Systems and methods for prescribing athletic activity to be performed by a user, and for adapting the prescribed athletic activity based on completed (e.g. ongoing) athletic performances by the user. A coaching plan may be automatically created that prescribes personalized athletic activities as a user trains towards a goal date. The athletic information may be received from one or more sensor devices associated with a user, and the coaching plan may be continuously or intermittently updated based on the received sensor data.

19 Claims, 19 Drawing Sheets

Related U.S. Application Data filed on Jun. 22, 2016, provisional application No. 62/308,766, filed on Mar. 15, 2016, provisional application No. 62/308,749, filed on Mar. 15, 2016.

(51) Int. Cl.

| | | |
|---|---|---|
| *G16H 20/30* | (2018.01) | |
| *A43B 3/00* | (2006.01) | |
| *A43B 5/00* | (2006.01) | |
| *A63B 71/06* | (2006.01) | |
| *G06N 3/04* | (2006.01) | |
| *G06N 3/08* | (2006.01) | |
| *A41D 1/00* | (2018.01) | |
| *G06N 20/00* | (2019.01) | |

(52) U.S. Cl.
CPC ...... *A63B 24/0003* (2013.01); *A63B 24/0062* (2013.01); *A63B 24/0075* (2013.01); *A63B 71/0622* (2013.01); *G06N 3/04* (2013.01); *G06N 3/0472* (2013.01); *G06N 3/08* (2013.01); *G16H 20/30* (2018.01); *A63B 2071/0625* (2013.01); *A63B 2071/0655* (2013.01); *A63B 2220/12* (2013.01); *A63B 2220/34* (2013.01); *A63B 2220/40* (2013.01); *A63B 2220/50* (2013.01); *A63B 2220/51* (2013.01); *A63B 2220/72* (2013.01); *A63B 2220/803* (2013.01); *A63B 2220/836* (2013.01); *A63B 2225/50* (2013.01); *A63B 2230/06* (2013.01); *A63B 2230/50* (2013.01); *G06N 20/00* (2019.01)

(58) Field of Classification Search
CPC ............ A63B 24/0003; A63B 24/0062; A63B 71/0622; A63B 2071/0625; A63B 2071/0655; A63B 2220/12; A63B 2220/34; A63B 2220/40; A63B 2220/50; A63B 2220/51; A63B 2220/72; A63B 2220/803; A63B 2220/836; A63B 2225/50; A63B 2230/06; A63B 2230/50; A41D 1/002; A43B 3/0005; A43B 5/00; G06F 19/3481; G06N 3/04; G06N 3/0472; G06N 3/08; G06N 20/00
USPC ....................................................... 434/247
See application file for complete search history.

(56) References Cited

U.S. PATENT DOCUMENTS

| | | |
|---|---|---|
| 2003/0204412 A1 | 10/2003 | Brier |
| 2009/0069156 A1 | 3/2009 | Kurunmaki et al. |
| 2013/0339409 A1* | 12/2013 | Kallio ............... G06F 1/163 708/100 |
| 2014/0122387 A1 | 5/2014 | Chi et al. |
| 2014/0277633 A1* | 9/2014 | Flaction ............... G16H 40/63 700/91 |
| 2016/0213976 A1* | 7/2016 | So ............... A63B 71/0622 |

FOREIGN PATENT DOCUMENTS

| | | |
|---|---|---|
| CN | 103336899 A | 10/2013 |
| CN | 104490388 A | 4/2015 |
| CN | 104880197 A | 9/2015 |
| CN | 105169620 A | 12/2015 |
| CN | 205031267 U | 2/2016 |

OTHER PUBLICATIONS

D C. Clarke et al.: "Rationale and resources for teaching the mathematical modeling of athletic training and performances", Advances in Physiology Education, vol. 37, No. 2 Jun. 1, 2013 (2013-06-01), pp. 134-152, XP055380347, US Issn: 1043-4046, DOI: 10.1152/advan.00078.2011 p. 134, col. 1 - p. 139, col. 2 figures 4, 7, 8, p. 140, col. 1 - p. 145, col. 2, p. 147, col. 1 - p. 148, col. 2.
Jul. 4, 2017 - (WO) Isr & WO - App. No. PCT/US17/022547 (225127.02634).
Jul. 4, 2017 - (WO) Isr & WO - App. No. PCT/US17/022565 (225127.02652).
Jul. 4, 2017 - (WO) Isr & WO - App. No. PCT/US17/022560 (225127.02636).
Clarke, David C., etc. "Rationale and resources for teaching the mathematical modeling of athletic training and performance" (Advances in Physiology education), 20130601.
Wikipedia "Collaborative filtering". Available online Mar. 1, 2014. Published by Wikipedia.org. Accessed Jan. 4, 2019 from <https://web.archive.org/web/20140301121611/https://en.wikipedia.org/wiki/Collaborative_filtering>.

\* cited by examiner

| level | days_per_week | Day 0 | Day 1 | Day 2 | Day 3 | Day 4 | Day 5 | Day 6 | Day 7 | Day 8 | Day 9 | Day 10 | Day 11 | Day 12 | Day 13 |
|---|---|---|---|---|---|---|---|---|---|---|---|---|---|---|---|
| BEGINNER | 2-3 | Kick it Off | | BM | | | | | Recovery | | Tempo | | | | |
| INTERMEDIATE | 2-3 | Kick it Off | | BM | | | Long | | Recovery | | Tempo | | | | |
| ADVANCED | 2-3 | Kick it Off | | BM | | | Long | | Recovery | | Tempo | | | | |
| BEGINNER | 3-4 | Kick it off | | BM | | Recovery | Long | | Recovery | | Tempo | | | | |
| INTERMEDIATE | 3-4 | Kick it off | | BM | | Recovery | Long | | Recovery | | Tempo | | | | |
| ADVANCED | 3-4 | Kick it off | | BM | | Recovery | Long | | Recovery | | Tempo | | | | |
| BEGINNER | 4-5 | Kick it off | | BM | Recovery | Recovery | Long | | Tempo | Recovery | | Interval | | | |
| INTERMEDIATE | 4-5 | Kick it off | | BM | Recovery | Recovery | Long | | Tempo | Recovery | | Interval | | | |
| ADVANCED | 4-5 | Kick it off | | BM | Recovery | Recovery | Long | | Tempo | Recovery | | Interval | | | |
| BEGINNER | 5-6 | Kick it off | Recovery | BM | Recovery | Recovery | Long | | Tempo | Recovery | Recovery | Interval | Recovery | Long | |
| INTERMEDIATE | 5-6 | Kick it off | Recovery | BM | Recovery | Recovery | Long | | Tempo | Recovery | Recovery | Interval | Recovery | Long | |
| ADVANCED | 5-6 | Kick it off | Recovery | BM | Recovery | Recovery | Long | | Tempo | Recovery | Recovery | Interval | Recovery | Long | |

| x (mi./wk) | level | Long (min.) | Tempo (min.) | Recovery (min.) | Interval (reps X meters w/ secsOfRest) |
|---|---|---|---|---|---|
| 0 | BEGINNER | 20 | 7 | 10 | 4 x 400 w/120" |
| 0 < x < 5 | BEGINNER | 20 | 7 | 10 | 4 x 400 w/120" |
| 5 <= x < 10 | BEGINNER | 20 | 7 | 12 | 4 x 400 w/120" |
| 10 <= x < 15 | INTERMEDIATE | 30 | 10 | 15 | 5 x 400 w/120" |
| 15 <= x < 20 | INTERMEDIATE | 35 | 10 | 20 | 5 x 400 w/120" |
| 20 <= x < 25 | INTERMEDIATE | 40 | 10 | 25 | 5 x 400 w/120" |
| 25 <= x < 30 | INTERMEDIATE | 45 | 10 | 30 | 5 x 400 w/120" |
| 30 <= x < 40 | ADVANCED | 50 | 15 | 35 | 6 x 400 w/120" |
| 40 <= x < 50 | ADVANCED | 55 | 15 | 40 | 6 x 400 w/120" |
| 50 <= x < 60 | ADVANCED | 60 | 15 | 45 | 6 x 400 w/120" |
| 60 <= x < 70 | ADVANCED | 65 | 20 | 50 | 6 x 400 w/120" |
| 70 <= x < 80 | ADVANCED | 70 | 20 | 55 | 6 x 400 w/120" |
| 80 <= x < 90 | ADVANCED | 75 | 25 | 60 | 6 x 400 w/120" |
| x >= 90 | ADVANCED | 80 | 25 | 65 | 6 x 400 w/120" |

FIG. 13B

ADAPTIVE ATHLETIC ACTIVITY PRESCRIPTION SYSTEMS

CROSS-REFERENCE TO RELATED APPLICATIONS

This application claims priority to U.S. Provisional Application No. 62/308,749, filed Mar. 15, 2016, U.S. Provisional Patent Application No. 62/308,766, filed on Mar. 15, 2016, U.S. Provisional Patent Application No. 62/353,394, filed Jun. 22, 2016, and U.S. Provisional Patent Application No. 62/368,559, filed Jul. 29, 2016, which are expressly incorporated herein by reference in their entireties for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling. Devices for tracking a user's activity may offer motivation in this regard, providing feedback on past activity, and encouragement to continue with an exercise routine in order to meet various exercise goals.

Still other people may be eager to train towards an athletic goal, such as a race, but may be limited to rigid training plans that are not tailored to their specific requirements and abilities (e.g. schedule, fitness level etc.), or training plans that have a significant lag between, and a limited number of adjustments based on the progress of a user.

BRIEF SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Aspects relate to methodology for prescribing athletic activity to be performed by a user, and for adapting the prescribed athletic activity based on completed (e.g. ongoing) athletic performances by the user. Systems and methods may be utilized to create a coaching plan that prescribes personalized athletic activities as a user trains towards a goal date. This coaching plan may include a running plan. In one example, athletic information may be received from one or more sensor devices associated with a user. The received athletic information may include historical, demographic, performance and/or other forms of data relating to the athlete. The athletic information may originate or be received from one or more sources and/or be obtained at different times and/or intervals.

BRIEF DESCRIPTION OF THE DRAWINGS

FIG. 13B is an example running plan that may be prescribed for a first two weeks of a running coaching plan, according to one or more aspects described herein;

Further, it is to be understood that the drawings may represent the scale of different component of one single embodiment; however, the disclosed embodiments are not limited to that particular scale.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
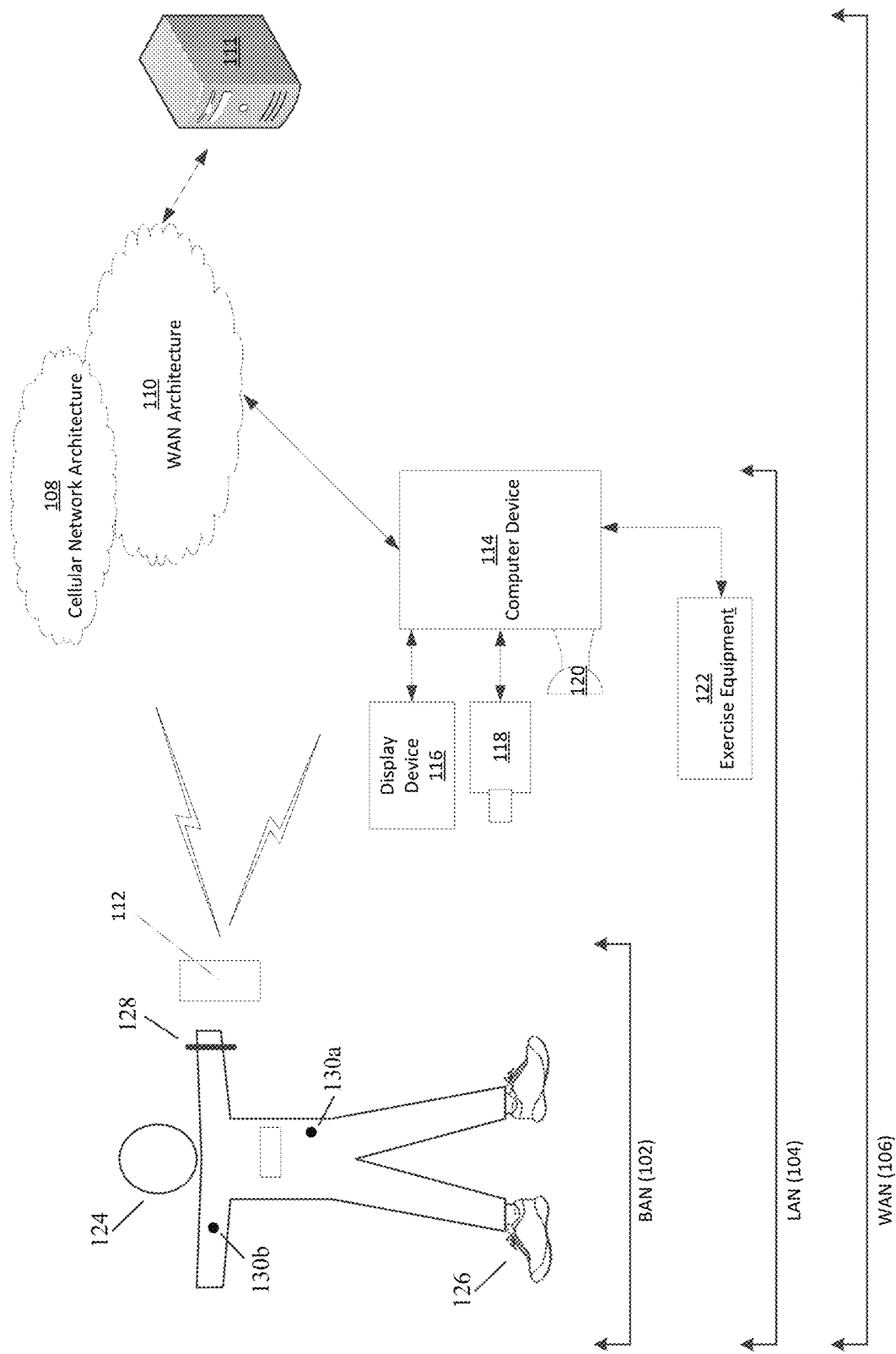
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
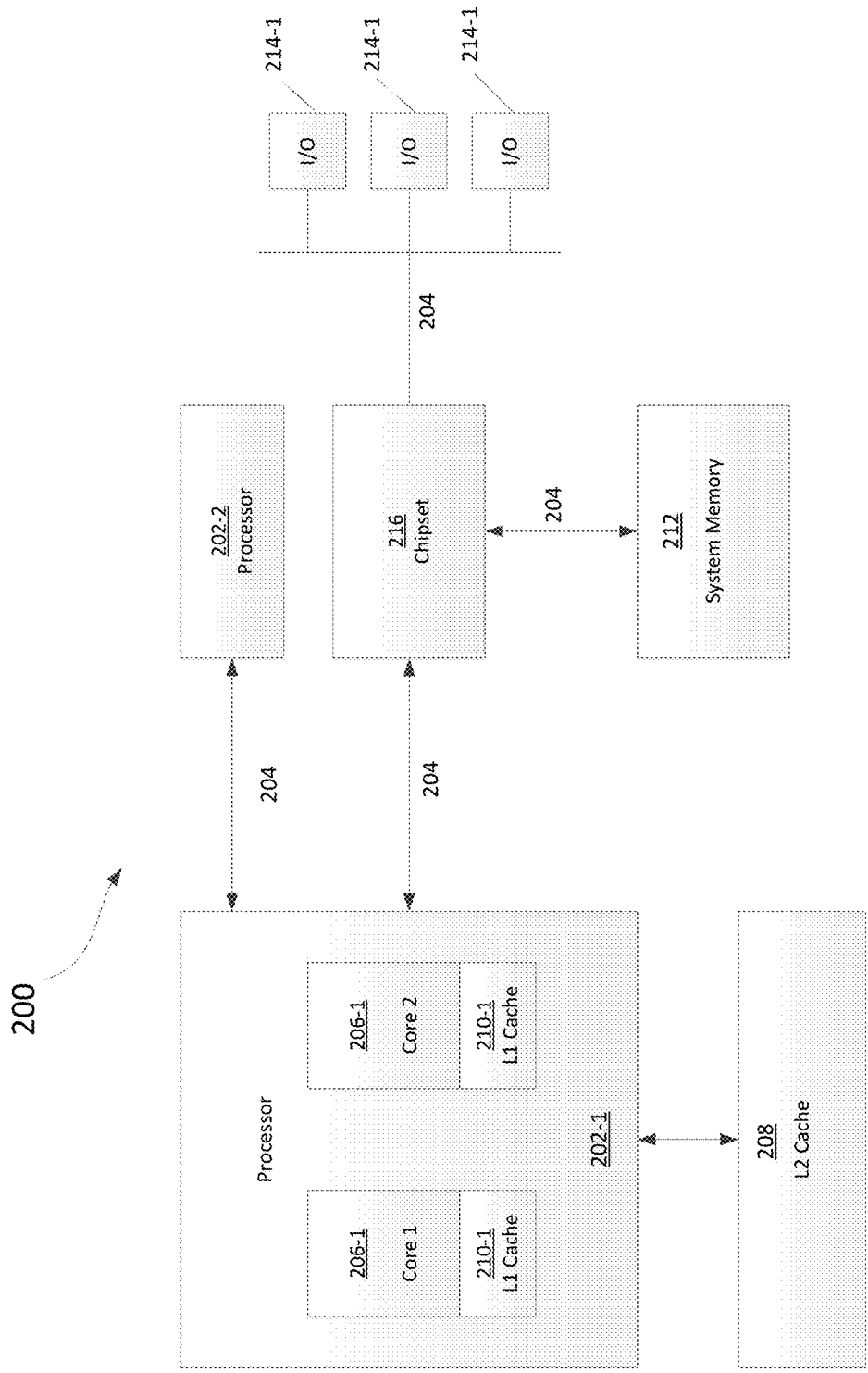
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
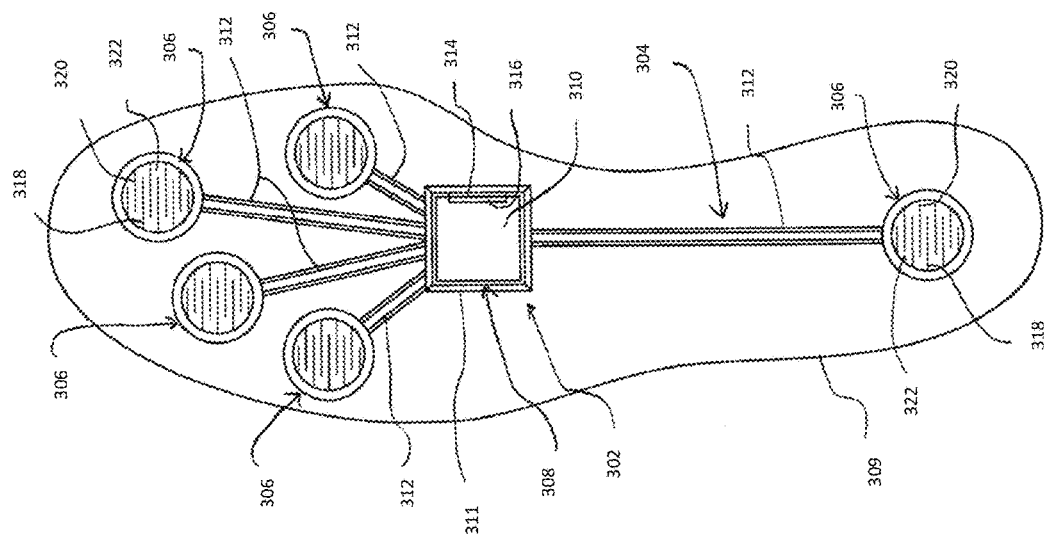
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
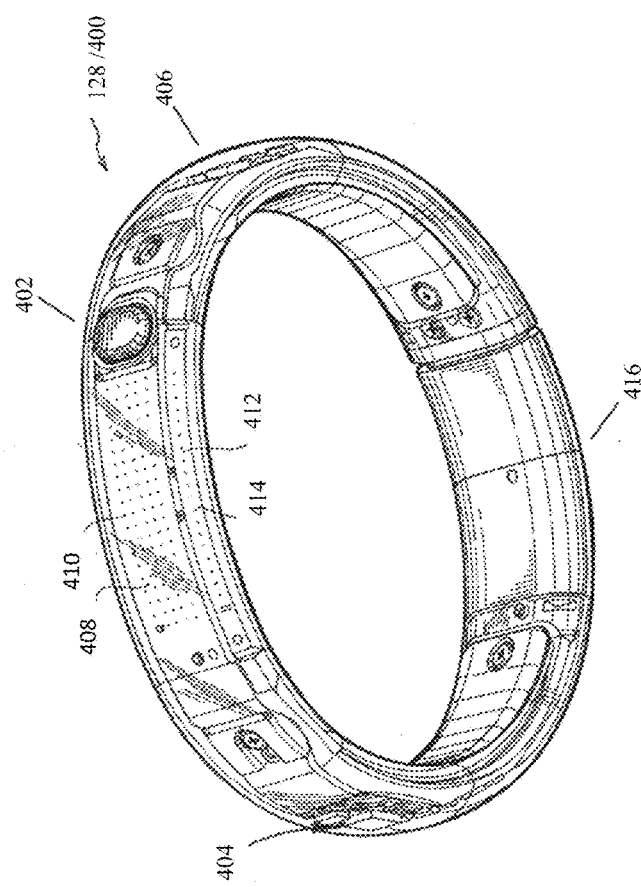
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130*a* and 130*b* may be sensors integrated into apparel, such as athletic clothing. Such sensors may be placed at any desired location of the body of user 124. Sensors 130*a/b* may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
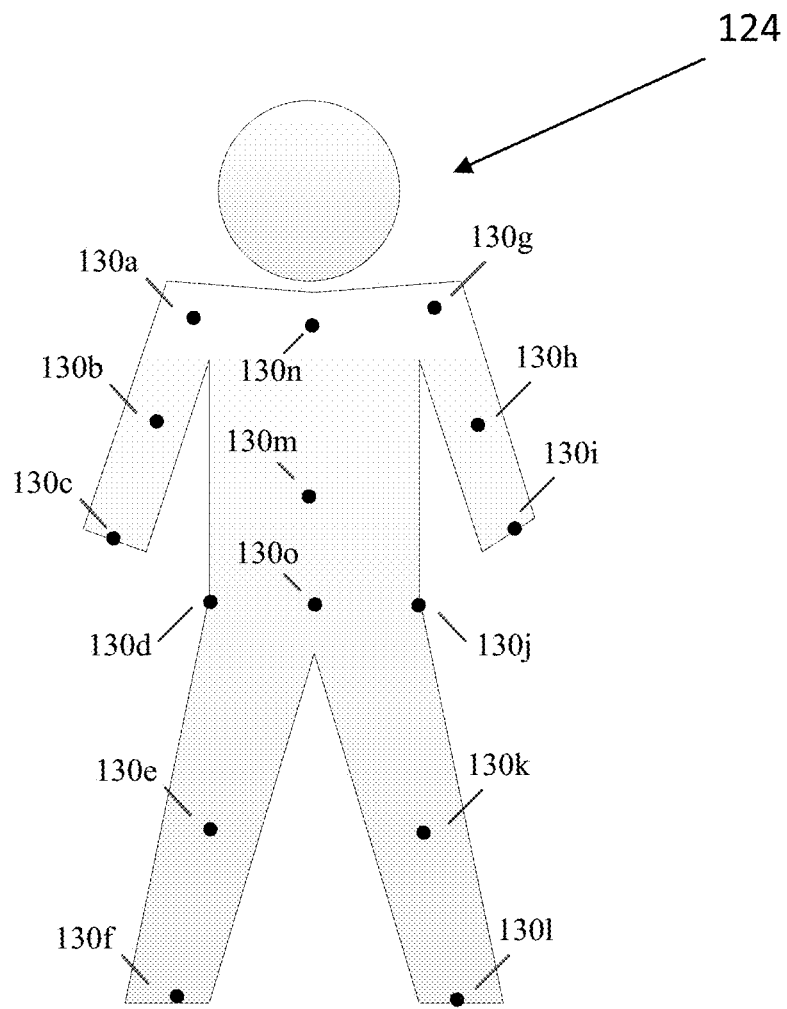
FIG. 5 shows illustrative locations for sensory input which may include physical sensors located on/in a user's clothing and/or be based upon identification of relationships between two moving body parts of the user come according to one or more aspects described herein.

FIG. 5 shows illustrative locations for sensory input (see, e.g., sensory locations 130*a*-130*o*). In this regard, sensors may be physical sensors located on/in a user's clothing, yet in other embodiments, sensor locations 130*a*-130*o* may be based upon identification of relationships between two moving body parts. For example, sensor location 130*a* may be determined by identifying motions of user 124 with an image-capturing device, such as image-capturing device 118. Thus, in certain embodiments, a sensor may not physically be located at a specific location (such as one or more of sensor locations 130*a*-130*o*), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130*m* may be utilized in a determination of the user's center of gravity (a.k.a, center of mass). For example, relationships between location 130*a* and location(s) 130*f*/130*l* with respect to one or more of location(s) 130*m*-130*o* may be utilized to determine if a user's center of gravity has been elevated along the vertical axis (such as during a jump) or if a user is attempting to "fake" a jump by bending and flexing their knees. In one embodiment, sensor location 1306*n* may be located at about the sternum of user 124. Likewise, sensor location 130*o* may be located approximate to the naval of user 124. In certain embodiments, data from sensor locations 130*m*-130*o* may be utilized (alone or in combination with other data) to determine the center of gravity for user 124. In further embodiments, relationships between multiple sensor locations, such as sensors 130*m*-130*o*, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130*m*-130*o* may serve as a point for a center of moment location of user 124. In another embodiment, one or more locations may serve as a center of moment of specific body parts or regions.

Overview of Example Athletic Activity Prescriptions

Aspects of the innovation relate to creating personalized athletic sequences which may be created based upon a user's experience level, desired outcome and/or focus, and be adaptive based upon the user's performance. Embodiments create a time-based adaptive coaching or training program. The program may output a calendar of prescribed athletic activities, which may or may not be positioned with one or more cycles within the prescribed plan. In one embodiment, the distribution of athletic activities may be created that are adaptive based upon a user's schedule, which may change during the prescribed plan of athletic activities.

It is known that a certain portion of the population enjoys conducting athletic activity as a regular part of their daily schedule and/or certain days or times of their weekly schedule. Prior art systems would not factor in this personal desire, and thus users would still conduct athletic activity during these days/times, which, since not factored into the non-adaptive prior systems, would predispose them to fatigue and/or injury. Further, other individuals may only have the time resources to conduct prescribed athletic activities 1-2 times per week or otherwise on a less frequent basis. Thus, for certain embodiments, it would be advantageous to ensure those users obtain the highest training load (e.g. TRIMP value) workout plans when they have the time to invest. Thus, in one embodiment, the highest TRIMP values may be queued in order of decreasing value. This may also ensure that those who conduct the prescribed athletic activities every day will not receive TRIMP values as high as the first two (or other quantity) days.

Some users may like to conduct their hardest workout regimes on certain days, e.g., go to the gym or play an event every Tuesday. The best prescription may not initially have them working the hardest (or a certain threshold level of work) on that desired day. However, given the adjustable nature of the plan, as the model updates, it will become closer to their reality.

In certain embodiments, using past actual data collected from the athlete's performance of the prescribed athletic activity as well as prescribed athletic activity (e.g., 40, 50, and 30 TRIMPS scheduled on the following days), allows microcycle divisions to be more even. This further ensures that "hard workouts", for example, which may be measured by TRIMPS, are spread out over the entire plan or goal period while also holding physiological intent intact.

Figure 6:
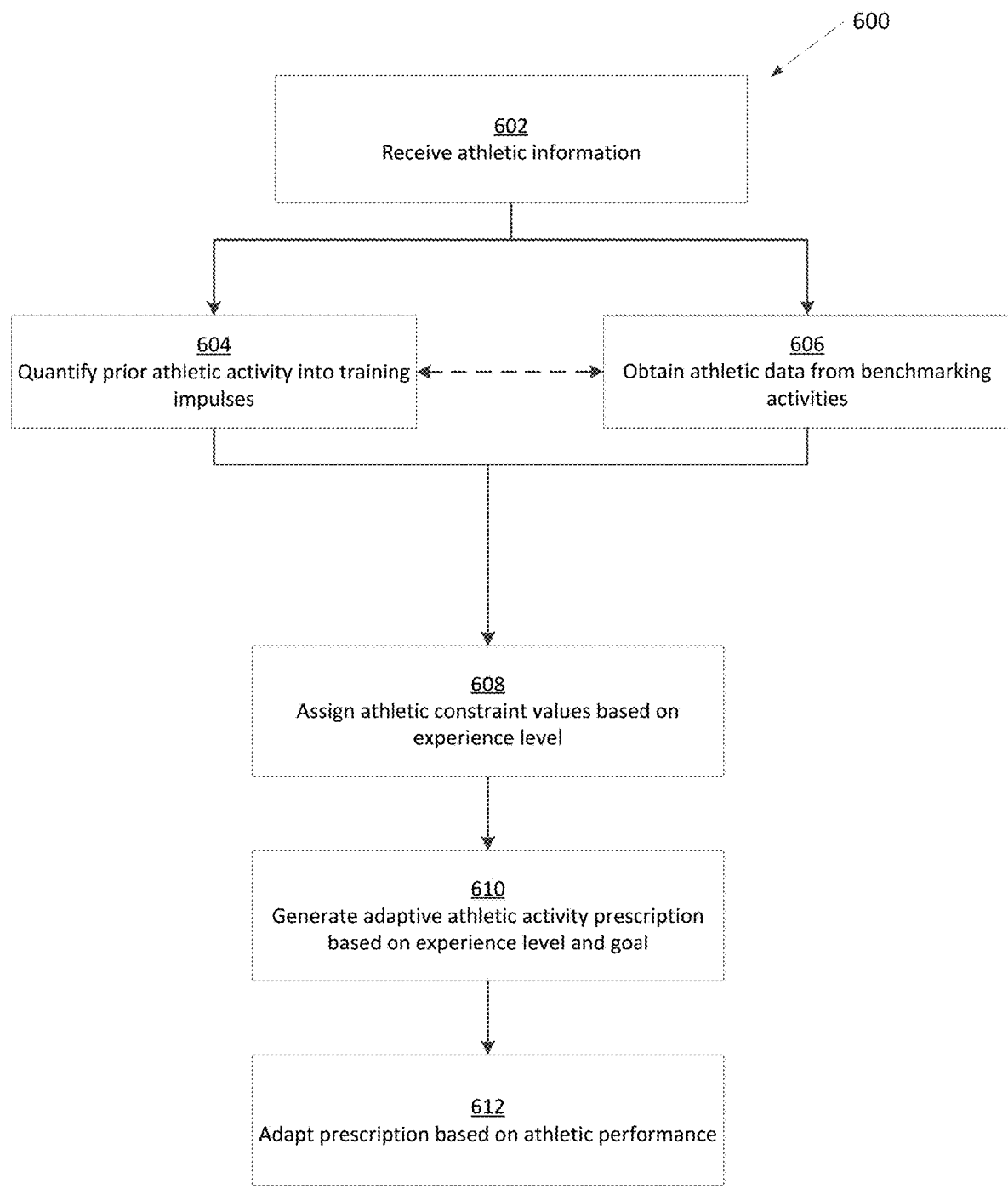
FIG. 6 is a flowchart diagram that describes methodology for prescribing athletic activity to be performed by a user, and for adapting the prescribed athletic activity based on completed athletic performances by the user, according to one or more aspects described herein.

FIG. 6 is a flowchart diagram 600 that describes methodology for prescribing athletic activity to be performed by a user, and for adapting the prescribed athletic activity based on completed (e.g. ongoing) athletic performances by the user. In one implementation, flowchart 600 may be utilized to create a coaching plan that prescribes personalized athletic activities as a user trains towards a goal date. This coaching plan may include a running plan, or a training plan. In one example, athletic information may be received from one or more sensor devices associated with a user. These one or more sensor devices may include any of the sensors previously described in this disclosure. The athletic information may be received, in one example, at block 602. The received athletic information may include historical, demographic, performance and/or other forms of data relating to the athlete. The athletic information may originate or be received from one or more sources and/or be obtained at different times and/or intervals. In one embodiment, demographic information, such as height, age, weight, and/or sex may be received. Received information may also include an indication of a goal date that may correspond to a competition date on which the user intends to participate in an athletic competition (e.g. a running race, such as a marathon date). In another example, a goal date may correspond to an intended end date of a coaching plan that may be adjustable (movable) in response to changes in a coaching plan. Received information may also include a number of days per week that the user intends to work out, a current level of activity of the user (e.g. an average number of miles run by the user per week, or an average number of hours spent training per week). Those skilled in the art will understand that one or more processors may process one or more received data values to generate additional or other athletic data.

In one example, one or more processes may be executed to quantify athletic activity completed by the user into one or more training expense metrics. A completed athletic activity may include, among others, a run, a cycle, a swim, a sports game (e.g. basketball, soccer, tennis, hockey, among many others), a gym training session. The completed athletic activity may be identified from sensor data received at block 602. In one implementation, a training expense metric may include a training impulse (otherwise referred to as a TRIMP)). In one example, quantification of prior athletic activity into training expense metrics, e.g. TRIMPs, may be executed at block 604. Further, one or more processes to quantify prior athletic activity into one or more training expense metrics are described in further detail later in this document.

In another example, a user may be instructed to complete one or more benchmark tests or activities. A benchmark test or activity may include an athletic activity with predefined constraints, such as a predefined time limit/duration, or a predefined distance. In particular, benchmark tests may include a three minute running test and a nine minute running test. For each of the three minute and nine minute running tests, a user may be instructed to run as far as possible within the allowed time. It is contemplated that benchmark tests prescribing different times than the three minute and nine minute tests may be utilized (e.g. a 1-minute, 2-minute, 4-minute, 5-minute, 6-minute, 7-minute, 8-minute, 10-minute, 11-minute running tests etc.), without departing from the scope of these disclosures. In one example, receiving athletic data from one or more benchmarking activities may be executed at block 606 of flowchart 600.

In an alternative example, a single benchmark test may be utilized at block 606 of flowchart 600. The single benchmark test may instruct a user to run as far as possible within a three minute time period. However, it is contemplated that different durations may be utilized (e.g. a 1-minute, 2-minute, 4-minute, 5-minute, 6-minute, 7-minute, 8-minute, 10-minute, 11-minute running tests etc.), without departing from the scope of these disclosures. As further described in FIG. 8B, the single benchmark test may be utilized to calculate a critical velocity for a user. Advantageously, a single benchmark test may allow the systems and methods described herein to calculate a coaching plan for a user using a more limited amount of information (e.g. without requiring two benchmark tests), thereby allowing a user to work quickly receive coaching information.

In one example, an instruction to complete a benchmarking test may be communicated to a user through an athletic activity device, such as one or more of those devices previously described herein. In another implementation, athletic activity data recorded by one or more sensor devices during non-benchmarking activities may be subsequently identified as appropriate for use as benchmarking data. It is noted that a benchmarking test may be prescribed to a user in addition to, or without obtaining past athletic data (e.g. without block 604). Further, a benchmarking test may be prescribed to the user based upon user preferences. For example, if a user wants to be coached to perform in a running-focused event, such as a 5K race, 10K race, half marathon or marathon (or an event with a running component, such as a triathlon), a running-specific benchmarking analysis may be conducted. In this regard, a benchmarking test prescribed to a user may include, among others, a 3-minute test during which a user is instructed to run as far as possible, a 9-minute test during which a user is instructed to run as far as possible, or a 3-minute all-out test. In certain embodiments, the results of two benchmarking tests (e.g. the 3-minute and 9-minute tests may be utilized to calculate a critical velocity and a finite work capacity for a user (described in further detail later in this document). In another embodiment, the result of a single benchmarking test (e.g. a 3-minute test during which a user is instructed to run as far as possible, or a 3-minute all-out test) may be utilized to calculate the critical velocity and finite work capacity for the user (described in further detail later in this document. See, e.g., FIG. 8B).

In one example, in order to calculate a coaching plan for a user, a user may be categorized into an experience classification. In one implementation, the user may be categorized into one of three experience classifications. For example, for a running athlete, the classifications may be defined as a beginner, intermediate, and advanced, and based upon a reported number of miles ran by the athlete on average during a week. In another example, for an athlete training using different exercises in a gym setting or otherwise, the athlete may be classified as a beginner, intermediate, or advanced based on a number of hours spent training on average during the week. However, it is contemplated that greater than or fewer than the three classifications may be utilized, without departing from the scope of these disclosures. In additional implementations, machine learning clustering algorithms may be utilized to classify users based on data associated with one or more users. For example, one or more machine learning clustering algorithms may be implemented using a database of user athletic information.

Further, in addition to, or as an alternative to the user input of an average number of miles run, or an average time spent training, the athlete may be categorized into an experience class based upon additional user input data, or athletic data sensed by one or more sensor devices. In one embodiment, the classification may be a single classification structure comprising a plurality of discrete categories, from which each categorized athlete is placed into a single category of the structure. In other embodiments, the classification structure may be multi-factorial. In certain embodiments, an athlete may be classified based upon a sport-specific and/or position-specific (of a sport) factor. In this regard, a user may, for example, be categorized as an experienced football player, but as a beginner tennis player. In another example, an athlete may be categorized as an experienced forward player for a given sport, but a beginner in the position of goalie for that same sport. The categories may be purely numerical, yet in other embodiments, they may be associated with text or symbolic strings, such as designating an experience level, which may range from beginner, intermediate, and/or advanced. Those skilled in the art will appreciate that these are merely examples and other quantities and/or qualitative properties may be utilized in accordance with various embodiments.

In one implementation, an experience level may be obtained from the athlete and/or other individuals (e.g., coaches, teammates, scouts), either directly, indirectly, via sensor data, and/or combinations of these and other sources. For example, if the athletic categorization relates to running, electronic data of the user's prior running experience may be analyzed from stored sensor data. In another implementation, the user's prior running experience may be analyzed based upon information manually inputted from the user, including a quantity of miles run, days running, distance, pace, and/or other data. In certain embodiments, including but not limited to using past sensor-obtained data, athletic data past a threshold time value may not be considered, and/or may be weighted differently than recent athletic data. For example, athletic data older than a month old may not be considered, or may be weighted differently than athletic data captured within the last month or other time frame. Further, although the above description utilizes a running example, it is contemplated that any sports, activity, or related athletic movements may be considered in the previously described an analysis.

In one implementation, upon categorizing a user into an experience category, one or more processes may be utilized to assign one or more athletic constants to the user, based upon the determined experience category. These one or more athletic constants may include, among others, a fitness gain, a fatigue gain, a fitness decay, and a fatigue decay. As will be described in further detail later, these athletic constants may be utilized to calculate a coaching plan for the user. Further, in one implementation, the one or more processes to categorize the user as well as to assign athletic constants to the user, based upon experience level of the user, may be executed at block 608 of flowchart 600 shown in FIG. 6.

An adaptive athletic activity prescription may be generated for a user based upon the categorized experience levels and a goal associated with the user. In one example, the goal associated with the user may be based upon user input, such as a target race day, or a target fitness level, among others. One or more outputs from processes to calculate the adaptive athletic activity prescription for a given user may include a prescribed athletic activity (e.g. a running distance and/or pace, or a training routine) that is prescribed for a specific day within a training program. In this way, the athletic activity prescription may include prescribed athletic activities for multiple days with prescribed rest days in between. In certain implementations, it will be appreciated that the adaptive athletic activity prescription, which may otherwise be referred to as a coaching plan, takes into account a large number of permutations of workout options available to a user, and as such, utilizes the computational speed of one or more modern computer processors capable of executing millions of calculations per second. The various processes executed to calculate an adaptive athletic activity prescription, or coaching plan, may be executed at block 610 of flowchart 600, and are described in further detail in relation to FIG. 6.

It is further contemplated herein that the athletic activity prescription, or coaching plan, calculated at block 610 may be adapted based upon changes associated with the athlete being coached. These changes may include changes to, among others, a user's fitness level (e.g. strength, speed, stamina, or balance, among others) as a result of the user completing one or more prescribed athletic activities, working out beyond prescribed athletic activities, or as a result of skipping or missing one or more prescribed athletic activities. In one implementation, an adaptation of a coaching plan may be executed at block 612 of flowchart 600, and may be executed based upon a manual user input, or may be executed automatically, based upon one or more detected changes (e.g. improvements, deteriorations, or deviations from an expected improvement to a user's fitness level). One or more processes utilized to adapt an athletic coaching plan are described later in this document. In one example, block 602 may be initiated upon receiving instructions to adapt a previously prescribed plan.

Example Collection of Athletic Information

Figure 7:
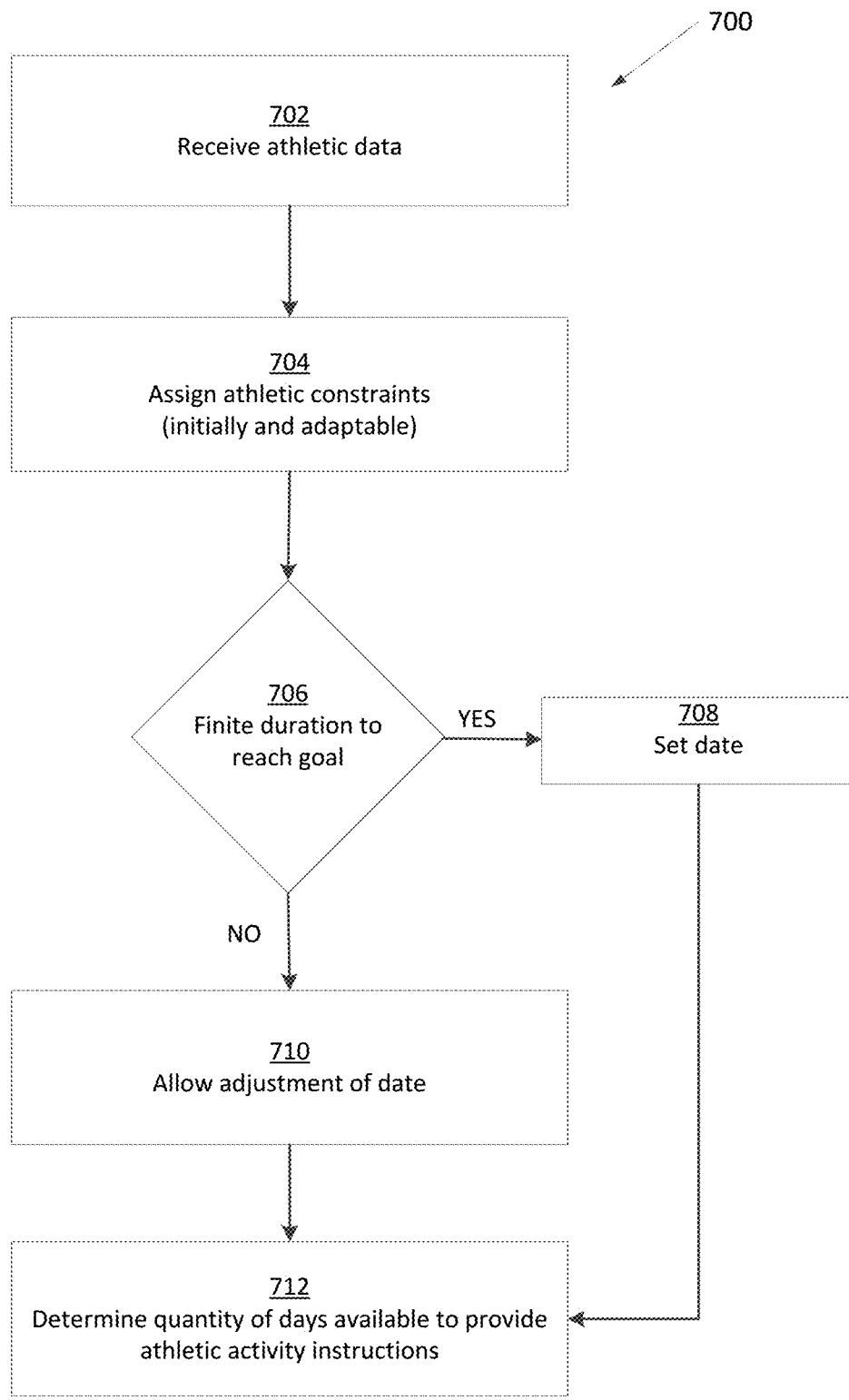
FIG. 7 is a flowchart diagram describing in further detail one or more processes of FIG. 6, according to one or more aspects described herein.

FIG. 7 is a flowchart diagram 700 describing in further detail one or more processes executed at block 602 of flowchart 600. One or more processes may be executed to receive athletic data from one or more sensor devices described herein or any other device capable of providing data (e.g., block 702). One or more systems or processes may be executed to receive user input data that includes a user's age, sex, height, weight, a target date to complete a coaching period on, a number of days that the user wants to workout per week, an amount of activity the user participates in (no. of mile run/hours spent training) during the week currently, among others. These one or more processes may be executed, in one example, at block 702. In one example, one or more initial athletic constants may be assigned to an athlete in response to received athletic data, e.g. at block 704. In one implementation, constant or variable numeric values that characterize the athlete's physiological response to fitness and/or fatigue may be assigned. In one embodiment, such parameters may include a non-linear dependence on time, the benefits of a tapering or peaking period, overtraining, and the plateau effect, among numerous others. Further, as discussed below, they may be utilized to predict performance.

These initial athletic values may be constants and include a fitness gain, a fatigue gain, a fitness decay, and a fatigue decay, among others. At an initial time point, such as the athlete's first use, before a predetermined quantity or quality athletic activity is captured after a specific time frame, completion of benchmarking is conducted, or combination thereof, one or more values may be assigned. The assignment (which may occur at block 704) may be default values and/or based upon one or more variables, such as the user's experience with the to-be-prescribed athletic activity, overall fitness or athleticism, age, weight, gender, and/or other combinations thereof. Later, once the athlete conducts benchmark analyses (e.g. see FIG. 8A detail), a set of constant values may specifically describe how they respond to training and/or are affected by fatigue. These personalized constants may later be calculated using a set of benchmarks which occur during the athlete's journey with an adaptive coaching system disclosed herein. In one embodiment, each athlete may be assigned one or more (e.g., all) of the following four constants:

$K1$=Fitness gain: the magnitude of positive effects (or fitness) an athlete will see from a single workout.

$K2$=Fatigue gain: the magnitude of negative effects (or fatigue) an athlete will see from a single workout.

$T1$=Fitness decay: time (e.g., a number of days) it takes for an athlete's positive effects from training (fitness) to dissipate.

$T2$=Fatigue decay: time (e.g., a number of days) it takes for an athlete's negative effects from training (fatigue) to dissipate.

Athletic constants may be assigned initially using bucketed normative data for athletes without a minimum of recent benchmarks, which may be for example more than 2, at least 4, or another value. Microcycle length may be calculated using the constant values in the systems and methods described herein (e.g. by one or more processes executed to provide an athletic training engine, as described in FIG. 6), but is shown in the below tables for simplicity.

It is also contemplated that athletic constants, including one or more of $K1$, $K2$, $T1$, $T2$ may be assigned to a user following classification of the user into an experience level classification, e.g. at block 608 of flowchart 600.

One or more processes may be executed to calculate a duration until a goal date. These one or more processes may, in one example, calculate the number of days between the current date and a goal date associated with a race date, or another date indicated by the user. In one implementation, calculation of a duration to reach a goal date may be executed at block 706. In one example, a date on which a to-be-prescribed adaptive coaching plan is to end may be set corresponding to a goal date specified by the user and/or received information. In another example, the date on which the adaptive coaching plan is to end may be set as another date before the date specified by the user. As such, one or more processes may be executed at block 708 to set the date. It is also contemplated that a user may manually adjust a calculated end date of the coaching plan to more specifically suit his/her schedule. Accordingly, the user may manually adjust this end date and/or may be adjusted from received data, either from the athlete's performance and/or from an external source, such as a rescheduled event (e.g., block 710). A quantity of days available to provide athletic activity instructions (e.g. a number of coaching days) may be determined at, in one example, block 712. Accordingly, the quantity of days available to provide athletic activity instructions may be calculated as, in one example: (number of days until a goal date)*(fraction of days per week a user is going to work out). Accordingly, in one example, a user may specify that he/she is willing to work out 4 days a week. As such, the fraction of days per week this example user is going to work out will be 4/7.

Calculating TRIMPS

Quantifying athletic activity or motions into TRIMPS may be utilized for one or more of: (1) quantifying prior athletic activity into TRIMPs; and (2) Determining the appropriate workout/athletic activity to prescribe for the athlete in an adaptive coaching system. The quantification will be generally described here in the context for block 604 of FIG. 6 described above, which is to quantify prior athletic activity, however, those skilled in the art will appreciate that the description is not so limiting.

Calculating Relative Intensity in Determining TRIMPS

Figure 8A:
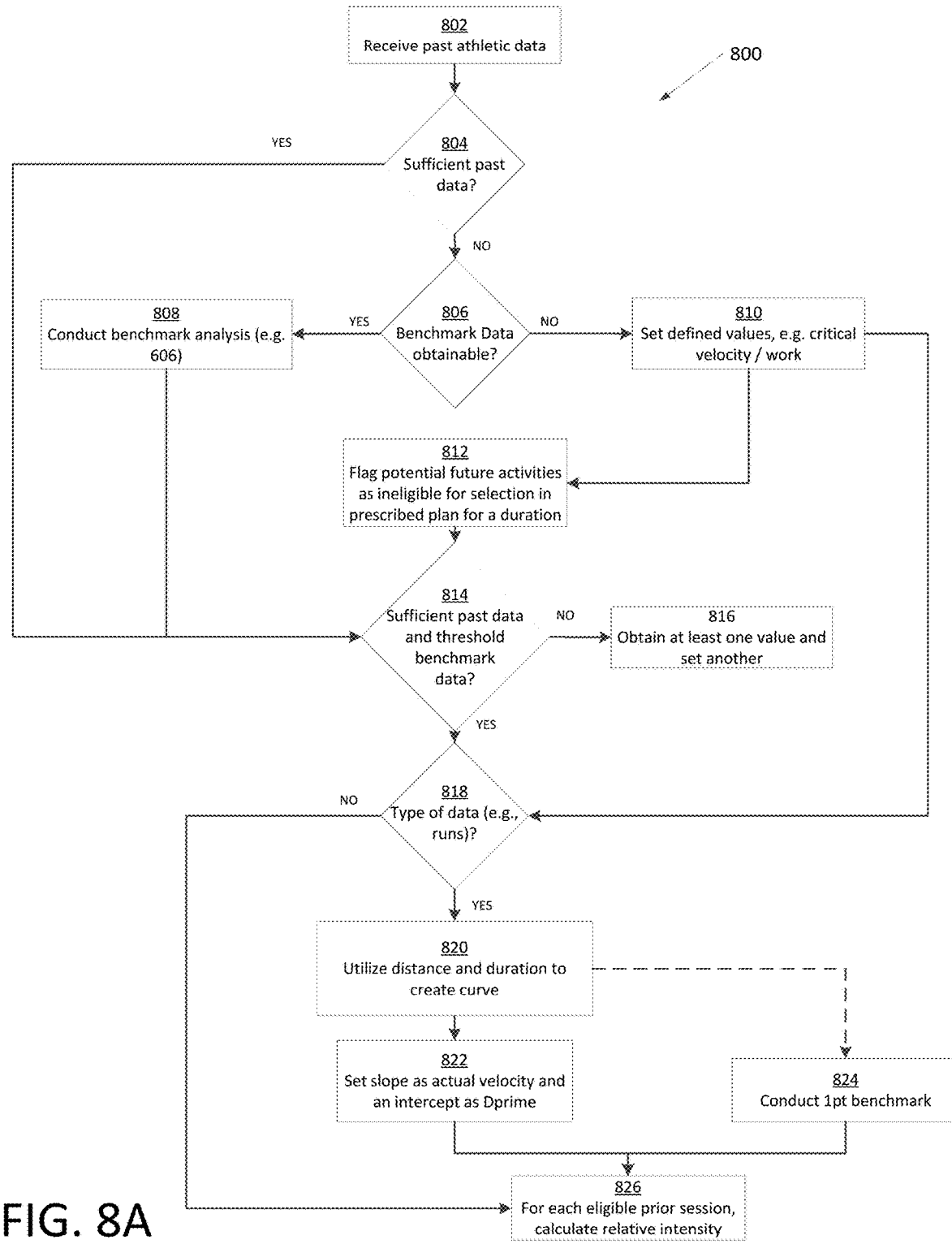
FIG. 8A is a flowchart diagram describing in further detail one example implementation of calculating relative intensity, according to one or more aspects described herein.

In accordance with certain embodiments, the calculation of TRIMPS may vary depending on one or more factors, including the athletic activity and/or the type of data available. In one embodiment, TRIMPS may be calculated from relative intensity. Relative intensity may be calculated differently based upon one or more factors, including but not limited to, the type of activity, the availability, quantity, and/or quality of athletic data, and/or preference. FIG. 8A is a flowchart diagram describing in further detail one example implementation of calculating relative intensity, which may be part of block 604 of FIG. 6. In particular, FIG. 8A describes one or more processes to calculate a number of training impulses associated with received athletic data. As such, athletic data may be received from one or more sensors, or may be manually inputted by a user.

Looking to flowchart 800 of FIG. 8A, this sensor data may be referred to as past athletic data, and may be received at block 802. One or more benchmark analyses may be executed on the received sensor data. Yet in other embodiments, benchmark workouts may be assigned to the specific athlete, either immediately and/or throughout the course of the prescribed athletic activity of the adaptive coaching system. For example, a user's performance, specific to a benchmark performance and/or past athletic data may be used as a domain-relevant benchmark to understand how TRIMPS affect performance. For example, a first benchmark activity, which may comprise a sequence of discrete activities, may be prescribed as part of the adaptive activity plans. In one embodiment, average power may represent a performance benchmark value for activity plans and one or more prescribed "Benchmark Workouts" may contain a known amount of "work" (e.g., defined in Joules). In one embodiment, the average Power is derived by dividing the defined Benchmark Workout work by the time it took the athlete to complete the workout.

The benchmark(s) can be user goal specific, sport-specific, position specific, and/or combinations thereof. In one embodiment, a performance benchmark may comprise an effort where the athlete covers as much distance as they can in a limited time. In one such implementation, an average speed is calculated by dividing the total distance covered in meters by the time. In one embodiment, the time may be less than 10 minutes. In another embodiment, the time is set to 3-minutes. The athlete's average speed may then represent or be utilized in determining the performance benchmark value. This implementation may be utilized if the user is preparing for a running event and/or the to-be-prescribed activity plan comprises a running element or focused on running.

Accordingly, one or more processes may be executed to determine, e.g. at block 804, if a sufficient amount of past data has been received. If a sufficient amount of data (which may be based on specific athletic data, e.g., running, playing world football etc., location data collected, time frame (e.g., only within past 2 weeks or within 4 weeks)) has not been received, the flowchart may proceed to block 806 to determine if data is obtainable from benchmarking workouts or routines. For example, past or recent benchmarking results may be utilized. Other embodiment may consider whether to administer a Benchmark Workout (see e.g., block 808) and/or include one or more Benchmark Workouts within a future date within the to-be-prescribed activity plan. If, in another example, an insufficient amount of past data has been received (e.g, at block 804) and adequate or acceptable data is not obtainable from a Benchmarking Workout (e.g., block 806), the flowchart may proceed to block 810, and predefined values may be assigned to the user based upon, among others, one or more of the user's age, sex, height, weight, a target date to complete a coaching period on, a number of days that the user wants to workout per week, an amount of activity the user participates in (no. of mile run/hours spent training) during the week currently. These predefined values may include, among others, a predefined critical speed and/or a predefined anaerobic work capacity (D') for the user.

One or more activities may be flagged as ineligible for selection by a user and/or available to be conducted in a prescribed adaptive coaching plan for a given duration, based upon the received past athletic data (or lack of data) and the user being associated predefined/default values for, among others, critical speed and anaerobic work capacity. As such, one or more activities may be flagged as ineligible for selection (e.g., block 812). Further, it is contemplated that the given duration during which the one or more activities are flagged as ineligible for selection may include any length of time, without departing from the scope of these disclosures. As one example, without knowing or otherwise having a threshold certainty or accuracy of an athlete's anaerobic work capacity (D' or dPrime), interval runs may be ineligible for selection or for performance.

In one example, if sufficient past data is obtained or otherwise available (with respect to at least one athletic parameter, however, a plurality of parameters may be required as well) for example at block 804, then the flowchart 800 of FIG. 8A may proceed to determine if a threshold level of benchmarking data has been obtained (e.g., such as prescribed and now performed Benchmark Workouts since the inception of a plan) (e.g., decision 814). As such, decision 814 may comprise one or more processes being executed to determine if a sufficient/threshold amount of data has been received from connected sensor devices associated with one or more athletic activities undertaken by the user, otherwise referred to as regular activity data, and to determine whether a threshold amount of benchmark data is stored for the user from one or more benchmarking tests undertaken by the user within a threshold amount of time prior to a current day. If there is insufficient benchmark data stored, for example, a threshold level of data is sufficient for a first value, however, not a second value, then the first value may be obtained and utilized, however, the second value may be set to a default value until more data is obtained (e.g., block 816). Accordingly, at least one athletic metric associated with the user may be received or calculated at block 816. In one example, if the to-be-prescribed adaptive workout plan or regime focuses on running, an average pace of the user may be calculated from specific Benchmark Workouts (e.g. runs) completed by the athlete. Further, at least one athletic metric associated with the user may be set equal to a default value at block 816. For example, a default value for anaerobic work capacity may be assigned to the athlete. For example, in a running focused workout plan, the anaerobic work capacity may be converted or otherwise transitioned to a distance the user would travel that represents their anaerobic workout capacity. In one embodiment, the initial value may be set to 200 meter.

If there is sufficient benchmark and regular activity data associated with athletic activities undertaken by the user stored in memory, in one implementation, one or more processes may be executed to check if the data (e.g. the regular activity data and/or the benchmark data) is associated with a specific activity, location, position, and/or captured with specific sensors. In one embodiment, it may be determined if the data comprises running athletic activities (e.g., decision 818). Those skilled in the art will realize that this is merely an example. Further, those skilled in the art will appreciate that running focused data may be filtered out from a larger collection of athletic data. If the data is associated with running athletic activities (e.g., at decision 818), one or more processes may be executed to calculate a critical velocity and/or an anaerobic work capacity for the user using only 1 data point and/or two or more data points. In this regard, novel systems and methods have been discovered by the inventors and disclosed herein for determining reliable critical velocity and anaerobic work capacity without as much psychological and physiological pressure being applied to the athlete as prior art methods. Such systems may allow the accurate determination of relative intensity from a plurality of different athletic performances.

In one example, the two data points may correspond to two separate runs completed by the user, with each data point comprising a distance traveled and the time taken to travel the distance. In one embodiment, the athlete may only be required to complete a single 3-minute run and a single 9-minute run. Such are only examples. In one example, one or more processes may be executed to calculate a slope of a line passing through the two running data points for the user when plotted (not required to be displayed) on a distance versus time graph (e.g., block 820). In one example, the two data points may correspond to two benchmarking test runs, e.g. a three minute and a nine minute benchmarking test run. It is contemplated, however, that any benchmarking test duration may be utilized, without departing from the scope of these disclosures. Accordingly, the critical velocity of the user may be calculated as a slope of a line. In one implementation, the slope of the line passing through the two data points when plotted on a distance versus time graph may be executed at block 820. In one example, a critical velocity for the user may be calculated as being equal to the slope of the line calculated at block 820. Additionally, the anaerobic work capacity for the user may be calculated as the intercept of the line passing through the two data points, such as the Y intercept. e.g. as block 822

In another implementation, one or more of a critical velocity and an anaerobic work capacity for the user may be calculated from a single benchmarking test data point. In particular, a user may be instructed to undertake a three minute all-out test during which the user is instructed to run as quickly as possible for three minutes. In one example, a critical velocity for the user may be calculated as being equal to an average velocity over the final 30 seconds of the three minute all-out test. Further, an anaerobic capacity may be calculated as being equal to an area of the three minute all-out test data (when plotted on a speed versus time graph) above the calculated critical velocity. In one example, this one-point benchmark test data may be utilized to calculate a critical velocity and an anaerobic work capacity for the user at block 824.

Example embodiments for determining whether enough prior data and/or Benchmark Workout data have been received and determining Critical Velocity (CriticalVelocity) may be executed as:

IF athlete has no runs completed in a current adaptive coaching plan, such that it just started, then CriticalVelocity and dPrime may be selected from one or more data values stored on a computer-readable medium. In one embodiment, CriticalVelocity=3 m/s and dPrime=200; ELSE IF athlete has no benchmarks completed in current plan, then CriticalVelocity=total distance of all runs in current plan meters/total time of all runs in current plan seconds, and dPrime may be set to a value stored on a computer-readable medium. In one embodiment dPrime=200.

In certain embodiments, additional processes may further include:

If an athlete has two or more benchmarks within a defined threshold period of time, then those may be used to determine critical velocity (CriticalVelocity) and/or anaerobic work capacity (dPrime). For example, in one embodiment, ELSE IF athlete has a 3-min benchmark AND a 9-min benchmark IN the last 14 days, then CriticalVelocity=(distance covered in 9-min benchmark meters−distance covered in 3-min benchmark meters)/(9*60−3*60), in which dPrime=distance covered in 3-min benchmark meters−(critical Velocity*3*60)

In yet further embodiments, a single benchmark may be utilized. For example, the implementation may include, as one example: ELSE (for use if athlete has at least one past benchmark), then:

> CriticalVelocity=(distance covered in benchmark meters/((time of benchmark in seconds^ 0.918)*1.8677) and dPrime=distance covered in 3-min benchmark in meters−(critical Velocity*time of benchmark in seconds)

In one implementation, (e.g. at decision 818) it may be determined that the stored benchmark and regular activity data is not associated with specific activity (e.g., running data), or after specific data has been generated (e.g., critical velocity and/or anaerobic work capacity, such as at blocks 820-824), one or more processes may be executed to cal-culate relative intensity. In this regard, TRIMP calculations may be specific to a coaching model and/or be athletic domain specific. For example, a training coach and a running coach may not calculate the same TRIMP value for a 20 minute run since its overall effect on the athlete's goal varies between the two athletic domains. TRIMP calculations may combine some metric of relative intensity with the total duration of the athletic activity. Systems may be implemented to calculate an accurate measure of relative intensity. For example, speed may be used for activity that includes of running (or at least a percentage of running activity, and/or comprises a running focus) but not used for other calculations.

Figure 8B:
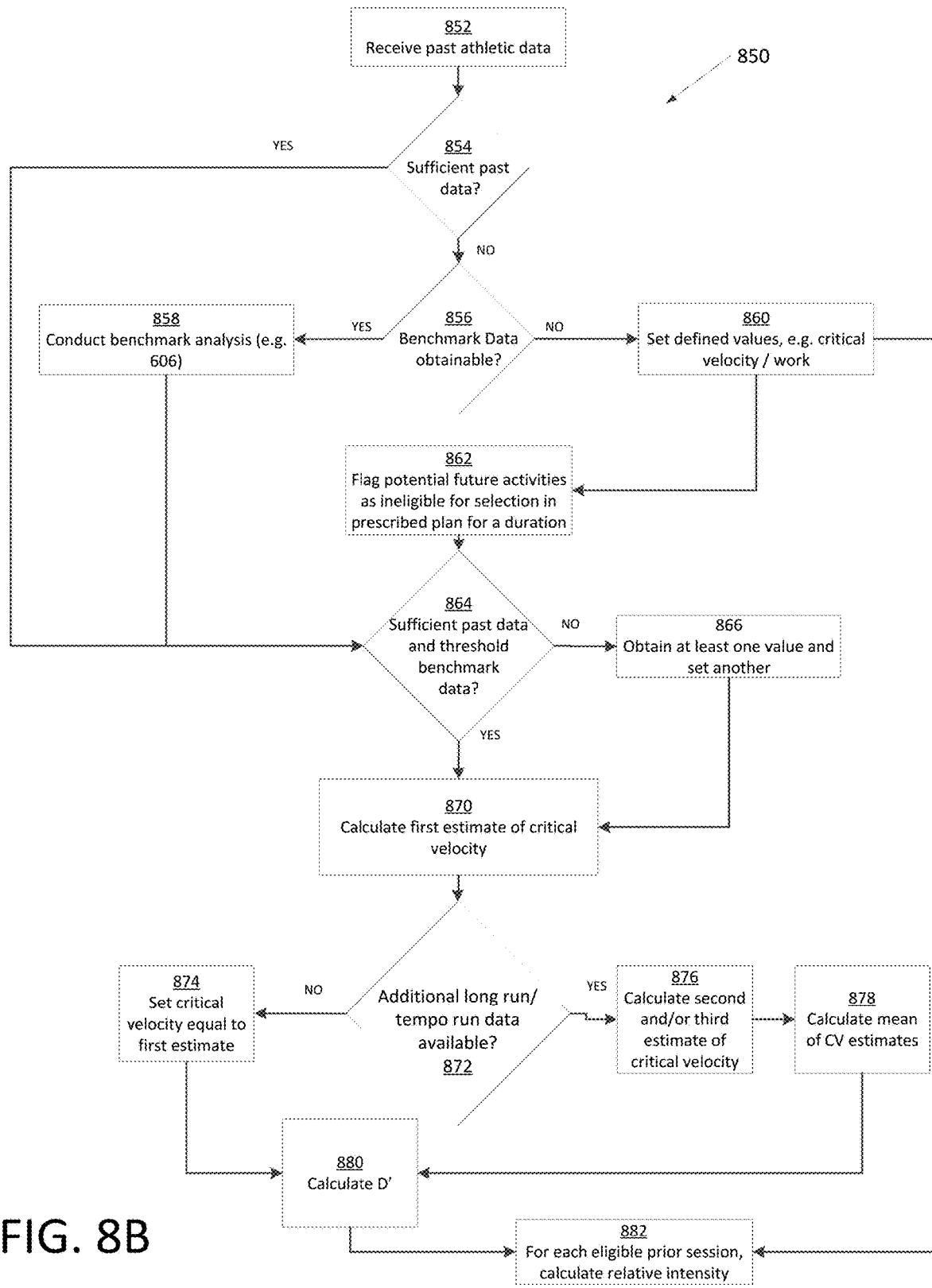
FIG. 8B is a flowchart diagram describing in further detail another example implementation of calculating relative intensity, according to one or more aspects described herein.

FIG. 8B is a flowchart diagram describing in further detail another example implementation of calculating relative intensity, which may be part of block 604 of FIG. 6. In particular, FIG. 604 describes one or more processes to calculate a number of training impulses associated with received athletic data. As such, athletic data may be received from one or more sensors, or may be manually inputted by a user.

Looking to flowchart 850 of FIG. 8B, this sensor data may be referred to as past athletic data, and may be received at block 852. One or more benchmark analyses may be executed on the received sensor data. Yet in other embodiments, benchmark workouts may be assigned to the specific athlete, either immediately and/or throughout the course of the prescribed athletic activity of the adaptive coaching system. For example, a user's performance, specific to a benchmark performance and/or past athletic data may be used as a domain-relevant benchmark to understand how TRIMPS affect performance. For example, a first benchmark activity, which may comprise a sequence of discrete activities, may be prescribed as part of the adaptive activity plans. In one embodiment, average power may represent a performance benchmark value for activity plans and one or more prescribed "Benchmark Workouts" may contain a known amount of "work" (e.g., defined in Joules). In one embodiment, the average Power is derived by dividing the defined Benchmark Workout work by the time it took the athlete to complete the workout.

The benchmark(s) can be user goal specific, sport-specific, position specific, and/or combinations thereof. In one embodiment, a performance benchmark may comprise an effort where the athlete covers as much distance as they can in a limited time. In one such implementation, an average speed is calculated by dividing the total distance covered in meters by the time. In one embodiment, the time may be less than 10 minutes. In another embodiment, the time is set to 3-minutes. The athlete's average speed may then represent or be utilized in determining the performance benchmark value. This implementation may be utilized if the user is preparing for a running event and/or the to-be-prescribed activity plan comprises a running element or focused on running.

Accordingly, one or more processes may be executed to determine, e.g. at block 854, if a sufficient amount of past data has been received. If a sufficient amount of data (which may be based on specific athletic data, e.g., running, playing world football etc., location data collected, time frame (e.g., only within past 2 weeks or within 4 weeks)) has not been received, the flowchart may proceed to block 856 to determine if data is obtainable from benchmarking workouts or routines. For example, past or recent benchmarking results may be utilized. Other embodiments may consider whether to administer a Benchmark Workout (see e.g., block 858) and/or include one or more Benchmark Workouts within a future date within the to-be-prescribed activity plan. If, in another example, an insufficient amount of past data has been received (e.g., at block 854) and adequate or acceptable data is not obtainable from a Benchmarking Workout (e.g., block 856), the flowchart may proceed to block 860, and predefined values may be assigned to the user based upon, among others, one or more of the user's age, sex, height, weight, a target date to complete a coaching period on, a number of days that the user wants to workout per week, an amount of activity the user participates in (no. of mile run/hours spent training) during the week currently. These predefined values may include, among others, a predefined critical speed and/or a predefined anaerobic work capacity (D') for the user.

One or more activities may be flagged as ineligible for selection by a user and/or available to be conducted in a prescribed adaptive coaching plan for a given duration, based upon the received past athletic data (or lack of data) and the user being associated predefined/default values for, among others, critical speed and anaerobic work capacity. As such, one or more activities may be flagged as ineligible for selection (e.g., block 862. Further, it is contemplated that the given duration during which the one or more activities are flagged as ineligible for selection may include any length of time, without departing from the scope of these disclosures. As one example, without knowing or otherwise having a threshold certainty or accuracy of an athlete's anaerobic work capacity (D'), interval runs may be ineligible for selection or for performance.

In one example, if sufficient past data is obtained or otherwise available (with respect to at least one athletic parameter, however, a plurality of parameters may be required as well) for example at block 854, then the flowchart 850 of FIG. 8B may proceed to determine if a threshold level of benchmarking data has been obtained (e.g., such as prescribed and now performed Benchmark Workouts since the inception of a plan) (e.g., decision 864). As such, decision 864 may comprise one or more processes being executed to determine if a sufficient/threshold amount of data has been received from connected sensor devices associated with one or more athletic activities undertaken by the user, otherwise referred to as regular activity data, and to determine whether a threshold amount of benchmark data is stored for the user from one or more benchmarking tests undertaken by the user within a threshold amount of time prior to a current day. If, there is insufficient benchmark data stored, for example, a threshold level of data is sufficient for a first value, however, not a second value, then the first value may be obtained and utilized, however, the second value may be set to a default value until more data is obtained (e.g., block 866). Accordingly, at least one athletic metric associated with the user may be received or calculated at block 866. In one example, if the to-be-prescribed adaptive workout plan or regime focuses on running, an average pace of the user may be calculated from specific Benchmark Workouts (e.g. runs) completed by the athlete. Further, at least one athletic metric associated with the user may be set equal to a default value at block 866. For example, a default value for anaerobic work capacity may be assigned to the athlete. For example, in a running focused workout plan, the anaerobic work capacity may be converted or otherwise transitioned to a distance the user would travel that represents their anaerobic workout capacity. In one embodiment, the initial value may be set to 200 meter.

If there is sufficient benchmark and regular activity data associated with athletic activities undertaken by the user stored in memory, in one implementation, one or more processes may be executed to check if the data (e.g. the regular activity data and/or the benchmark data) is associated with a specific activity, location, position, and/or captured with specific sensors. In one embodiment, it may be determined if the data comprises running athletic activities. Those skilled in the art will realize that this is merely an example. Further, those skilled in the art will appreciate that running focused data may be filtered out from a larger collection of athletic data. If the data is associated with running athletic activities, one or more processes may be executed to calculate a critical velocity and/or an anaerobic work capacity for the user using data from a single benchmark test (e.g. 3-minute benchmark test). In one example, only one data point obtained from the single benchmark test may be utilized to calculate a critical velocity for a user. In this regard, novel systems and methods have been discovered by the inventors and disclosed herein for determining reliable critical velocity and anaerobic work capacity without as much psychological and physiological pressure being applied to the athlete as prior art methods. Such systems may allow the accurate determination of relative intensity from a plurality of different athletic performances. In one embodiment, an athlete may complete a single 3-minute benchmark run. However, alternative durations may be utilized, without departing from the scope of these disclosures.

Figure 15A:
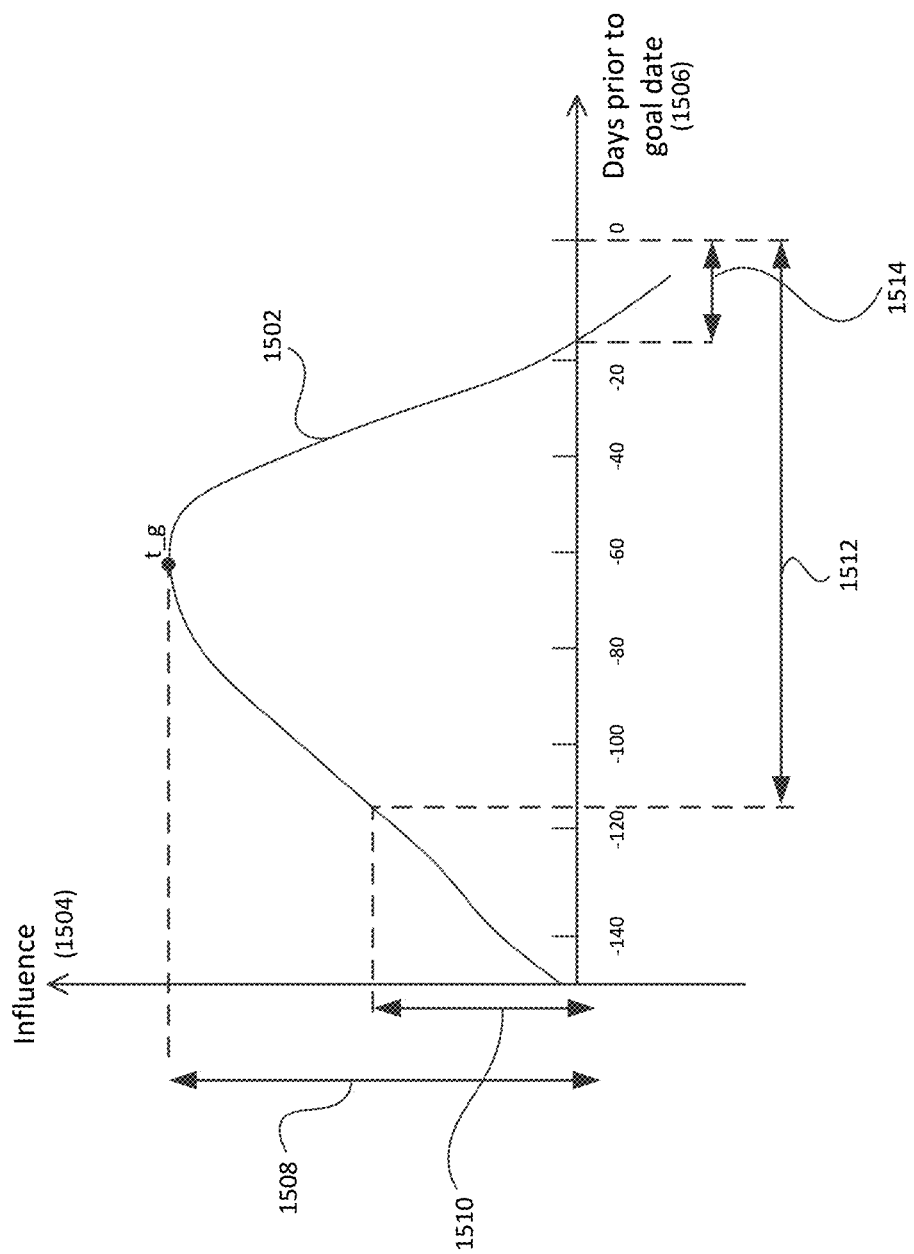
FIG. 15A schematically depicts an influence curve for a given user, according to one or more aspects described herein.
Figure 15B:
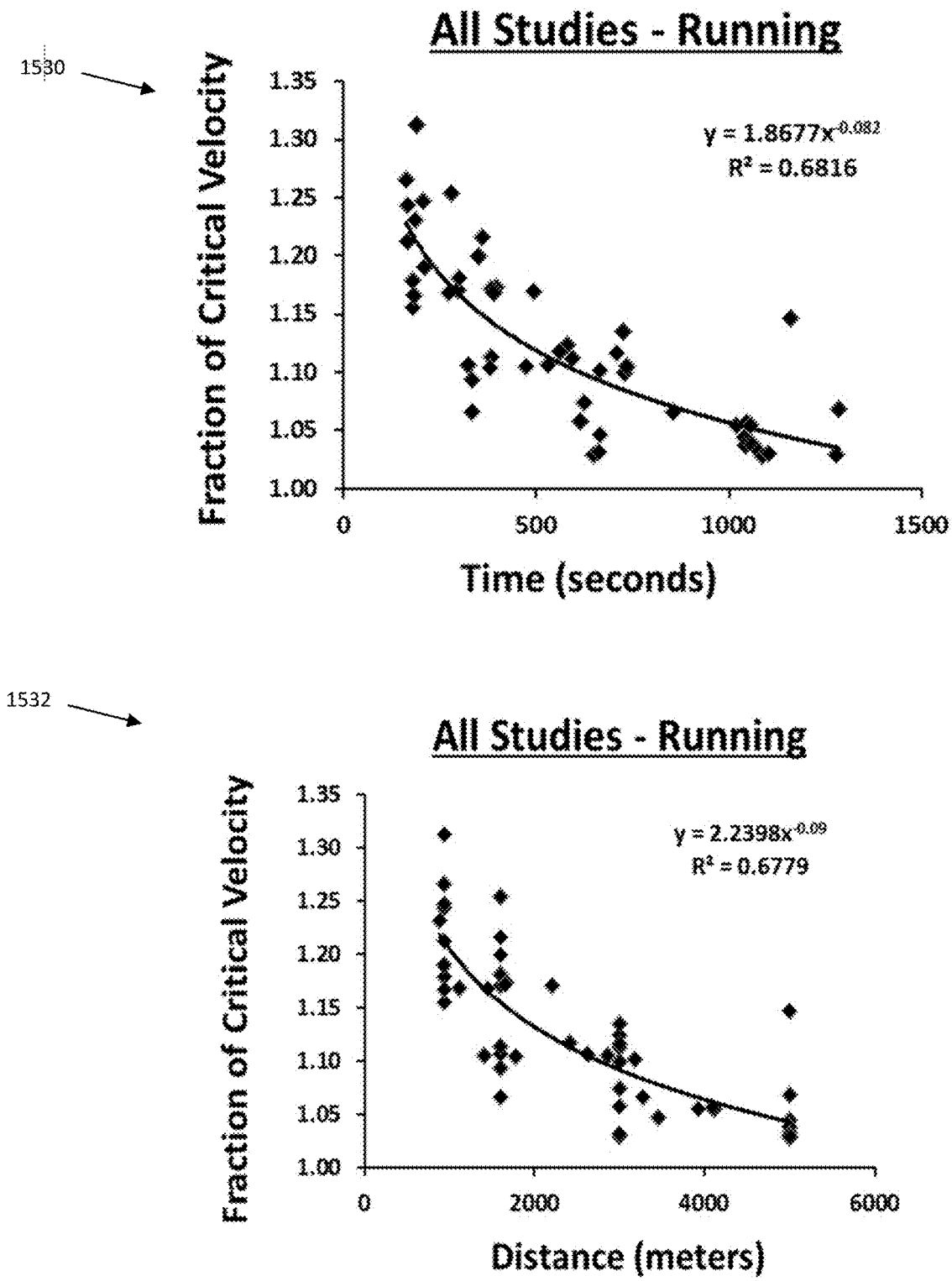
FIG. 15B depicts empirical data used to derived an equation for calculation of a critical velocity of a user, according to one or more aspects described herein.

In one example, a first estimate of a critical velocity of a user may be calculated at block 870 from data obtained during a single benchmark test. In particular, the first estimate of critical velocity may be calculated using: first estimate of Critical Velocity=(distance covered during single benchmark [expressed in meters]/((time of benchmark [expressed in seconds]^0.918)*1.8677) (Equation 1). The empirical data utilized to arrive at this equation is depicted in FIG. 15B.

If a user has completed additional run types and has data stored for those runs (tempo and long run types), then flowchart 850 may proceed from decision block 872 to block 876. If, however, no additional runs have been completed by the user in addition to the single benchmark test run, flowchart 850 may proceed from decision block 872, to block 874. In one example, data may only be valid if associated with a run completed within an eligibility window of seven days. However, it is contemplated that additional or alternative durations for the eligibility window may be utilized, without departing from the scope of these disclosures. For example, the eligibility window for stored running data may be two days, four days, five days, eight days, two weeks, among many others. At block 874, the critical velocity may be set equal to the first estimate a critical velocity of the user, as described above. At block 876, a second and/or a third estimate a critical velocity may be calculated from data generated during a tempo and/or a long run. Accordingly, in one example, the second estimate of critical velocity may be calculated from a tempo run (i.e. a run at anaerobic threshold) using the equation: second estimate of Critical Velocity=1.0*average velocity of user during the tempo run (Equation 2).

A third estimate of a critical velocity may be calculated from data generated during a long run, and utilizing the equation: third estimate of Critical Velocity=1.2*average velocity of user during the long run (Equation 3).

Figure 15C:
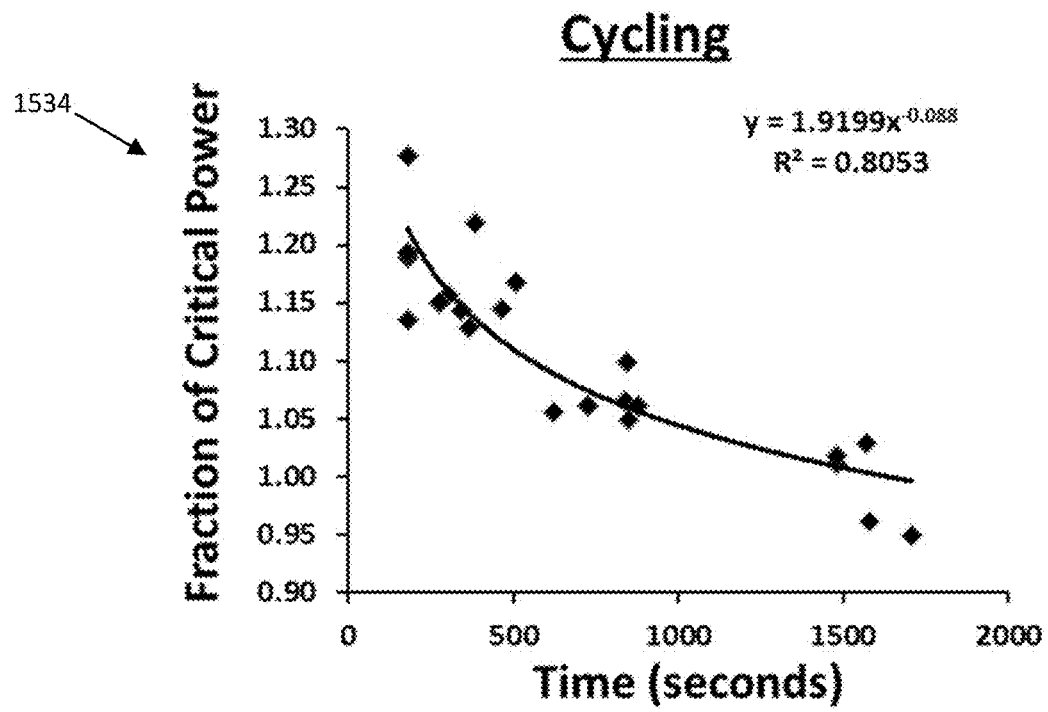
FIG. 15C depicts empirical data used to establish a relationship between different running pacing and distance prescriptions and critical velocity of a user, according to one or more aspects described herein.
Figure 15C:
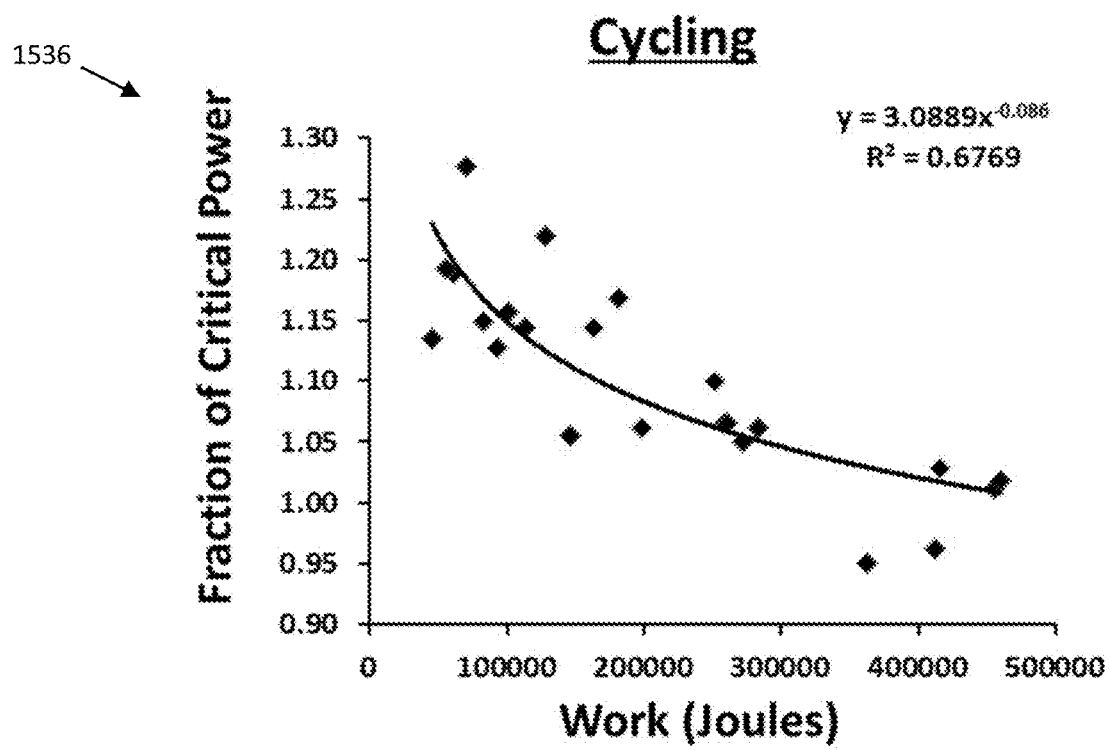

As such, it is found that a user runs above a critical velocity during a three minute benchmark test (first estimate of critical velocity at block 870), approximately equal to critical velocity during a tempo run (second estimate of critical velocity at block 876), and below critical velocity during a long run (third estimate a critical velocity at block 876). In one example, a user may run at approximately 83% of the user's critical velocity during a long run. However, a range of percentages may be utilized (e.g. approximately 80% to approximately 86% of critical velocity), without departing from the scope of these disclosures. FIG. 15C depicts results of empirical tests utilized to establish a relationship between different running pacing and distance prescriptions and critical velocity of a user. The 83% value is derived, in one example as an average from different methods for calculating critical velocity for an endurance run.

The critical velocity of the user may be calculated as an arithmetic mean of the first, and one or more of the second and/or third estimates of critical velocity (e.g. at block 878).

In one implementation, the anaerobic work capacity, otherwise referred to as D' or dPrime may be calculated from the value of critical velocity (critical Velocity) calculated at block 874 or block 878 as: DPrime=distance covered in 3-min benchmark in meters−(critical Velocity*time of benchmark in seconds).

One or more processes may be executed to calculate relative intensity. The one or more processes may be executed at block 882, and may calculate, in one example, a steadyStatePace (i.e. relative intensity variable)=a fraction of an average velocity during a run to the user's critical velocity. One or more processes to calculate relative intensity may be executed at block 882.

Figure 9:
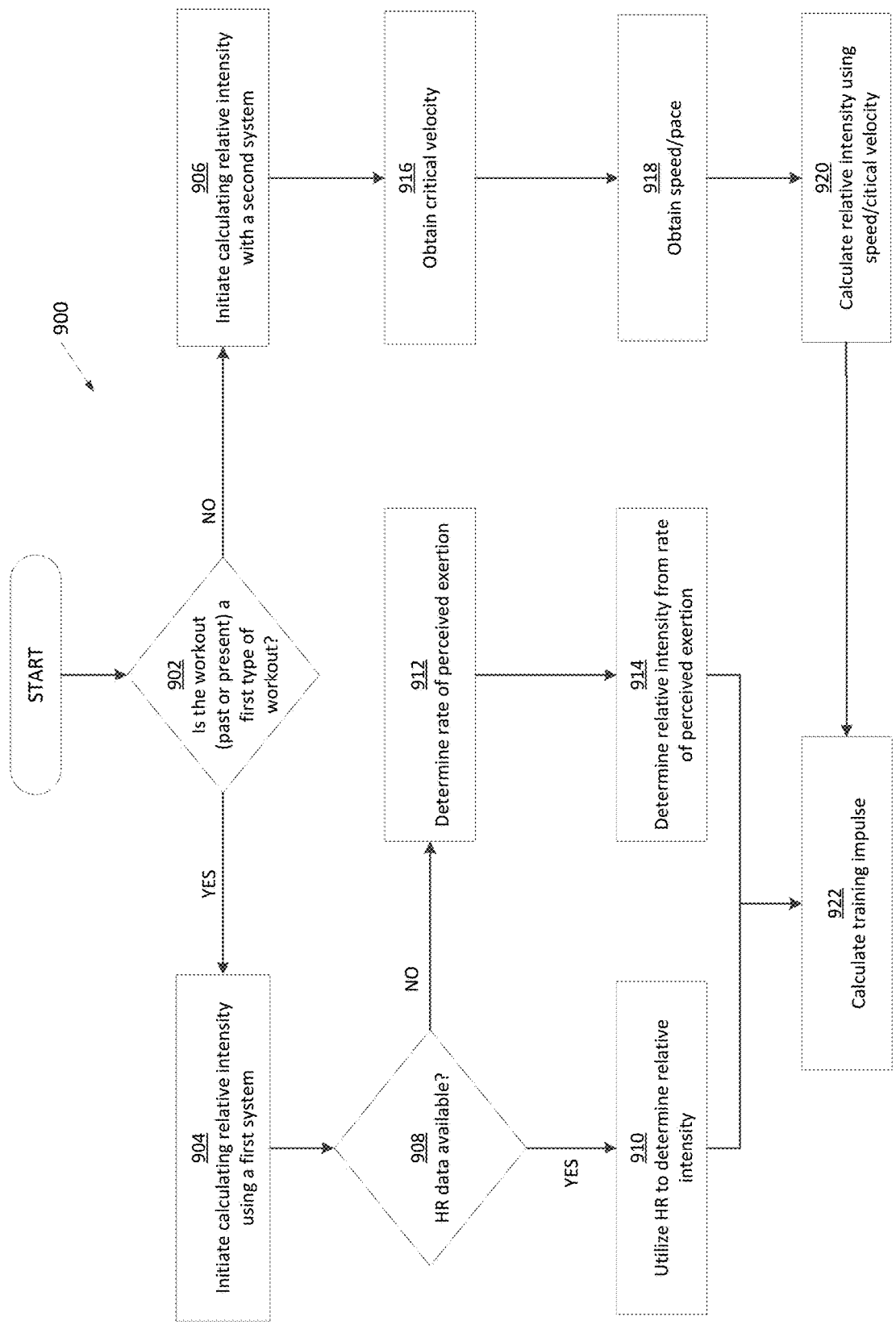
FIG. 9 is a flowchart diagram exhibiting an example embodiment of determining TRIMP using relative intensity calculated under different conditions, according to one or more aspects described herein.

In one implementation, multiple activity sessions associated with a given user/athlete may be stored in memory, based on received sensor data from one or more athletic activity sensor devices. In order to prescribe an adaptive activity coaching plan for a user, one or more athletic activity sessions completed by the user may be analyzed, and a relative intensity calculated using the athletic activity session data. The number of eligible prior sessions for which relative intensities are calculated may vary based upon, among others, the age of the data, or the type of coaching plan prescribed to the user. FIG. 9 shows flowchart 900 exhibiting an example embodiment of determining TRIM' using relative intensity (RI) calculated under different conditions. Flowchart 900 may include a decision whether to determine if the workout (either past workout or a to-be-prescribed) is a specific type of workout or class or activity. For example, it may be determined if the workout is a first type of workout (e.g., decision 902), such as a weight-training exercise. If so, calculating relative intensity is initiated using a first system (or process), such as shown at block 904. The first system may determine whether a first type of data is available, such as whether heart rate data is available (e.g., decision 908). If so, heart rate may be utilized to determine relative intensity (e.g., bock 910). Non limiting examples of using heart rate are provided below.

In other examples activity with a Rate of Perceived Exertion (RPE) assigned and/or assignable may be considered if specific data (e.g., heart rate data) is not available or is not adequate (e.g. block 912). In another implementation, Heart Rate (HR) data may be utilized for training routine or other activity. In one example, HR may be the default parameter utilized if such data or threshold level of data is available, for example, in which running is not a specific goal, percentage of the activity, and/or a threshold of running is not met. Certain implementations may determine if heart rate data is available (e.g., decision 908). In certain embodiments, systems may be configured to utilize RPE in the absence of HR or reliable HR data (e.g., 912).

In some embodiments, RPE may be determined by a user inputting a rate of perceived exertion following an exercise session. In one example, the rate of perceived exertion may be received as a number on a scale of 0 to 10. However, it is also contemplated that additional or alternative scales may be utilized with a rate of perceived exertion, without departing from the scope of these disclosures. The received rate of perceived exertion may be mapped to an oxygen consumption scale for the user, based upon a constructed athletic profile for the user. In one example, the scale of the rate of perceived exertion may be linearly mapped to a volume of oxygen consumption scale delimited by a maximal oxygen consumption estimated for the user based upon the calculated athletic profile for the user. In other implementations, nonlinear mappings of the rate of perceived exertion scale to the volume of oxygen consumption scale may be utilized, without departing from the scope of these disclosures. Additionally, one or more processes may be executed to output an estimated volume of oxygen consumption, based upon the inputted rate of perceived exertion of the user.

One or more of the above or other calculations may also consider athletic-specific information, such as, for example, received or calculated from block 602 and/or flowchart 700. For example, information relating to gender may be used, along with sensor data, such as heart rate (e.g., block 910) to determine relative intensity. In one example, if heart rate may be utilized to compare one of the resting heart rate, maximum heart rate and/or average heart rate. Such information can collectively or individually be used in the calculation of TRIMPS. Further, if gender is known, the TRIMP for an activity or prescribed for a set day (such as described below) may also be considered. A non-limiting example of an equation to calculate TRIMPS (e.g., at block 922 in which heart rate data is available, such as determined at decision 908) that may be utilized is Equation 4:

IF gender==male THEN $b$=1.92 ELSE $b$=1.67, and
IF gender==female THEN $k$=0.64 ELSE
$k$=0.86, in which     Equation 4:

totalDayTRIMP+=(activityDuration)*((avgHeartRate-restHeartRate)/(maxHeartRate-restHeartRate))*$k$*$e$^(((avgHeartRate-restHeartRate)/(maxHeartRate-restHeartRate))*$b$).

In embodiments in which RPE is selected or otherwise utilized in the determination of TRIMPS of an activity, the athlete's relative intensity may be derived from the RPE. (e.g, block 914 and block 922). The RPE may be derived (directly or indirectly) from a user input, and/or sensor data. The RPE may be multiplied by a constant in one embodiment, and yet other embodiments may utilize variables. A non-limiting example equation, such as Equation 5 may be used.

intensity=RPE*0.1     Equation 5:

And totalDayTRIMP+=activity-Duration*intensity*$k$*$e$^(intensity*$b$)

In one implementation, such uses may only be used when specific workout(s) are not associated with a run, and/or sensor data for at least one value reaches a threshold. In certain embodiments, this may provide a "NO" determination at decision 902). A second system (or process) may be implemented to initiate relative intensity (e.g., block 906 as compared with block 904). In one embodiment, an athlete's pace may be obtained or calculated and is not consistent enough to be considered a threshold pace or duration of threshold pace, or distance (e.g., at decision 902 being used to initiate block 906). In yet another embodiment, the user or other user (e.g., trainer) may flag the activity or day as not being a running or activity day. As discussed above, information, such as gender may be utilized and/or assigned a constant, which may be the same constant used above with respect to the above examples. In certain embodiments, the athlete's critical velocity (C.V.) may be obtained. In one embodiment, one or more systems or methods discussed in relation to one or more of blocks 820, 822 and/or 824 may be utilized to determine critical velocity. In yet further embodiments, a speed or pace may be utilized (e.g., block 918). In one embodiment, Relative intensity for specific activities may be:

Relative intensity=(normalized speed)/(critical velocity)      (Equation. 6)(e.g., block 920)

Accordingly, the normalized speed may be calculated as a weighted average of speeds of the user with higher speeds weighted more heavily than lower speeds. It is contemplated that any weighting multipliers may be utilized, without departing from the scope of this disclosure. In one implementation, the relative intensity for one or more eligible prior of athletic activity sessions (or determining TRIMPS of possible prescribed workouts) may be calculated at block 820 of flowchart. Additionally, a training impulse may be calculated using a relative intensity and a critical velocity for a given athlete. In one embodiment, it may be determined using the equation:

Training Impulse(TRIMP)=(relative velocity)*(duration)      (Equation. 7)

This may be implemented as part of blocks 920 and 922. As one example, an example implementation of at least a portion of flowchart 900 may include:

Critical Velocity=quantifyBenchmarks(activities)

FOR EACH day FROM start TO end OF planSchedule:
FOR EACH activity ON day:
IF activity IS run normalizedRunSpeed=classify(activity,critical Velocity)

totalDayTRIMP+=(normalizedRunSpeed^2)*activityDuration/((critical Speed^2)*36)

ELSE IF activityMetrics CONTAINS heartRate THEN totalDayTRIMP+=(activityDuration)*((avgHeartRate−restHeartRate)/(maxHeartRate−restHeartRate))*$k$*$e$^(((avgHeartRate−restHeartRate)/(maxHeartRate−restHeartRate))*$b$)

ELSE IF activityMetrics CONTAINS rpe THEN intensity=RPE*0.1 totalDayTRIMP+=activityDuration*intensity*$k$*$e$^(intensity*$b$)

Figure 10:
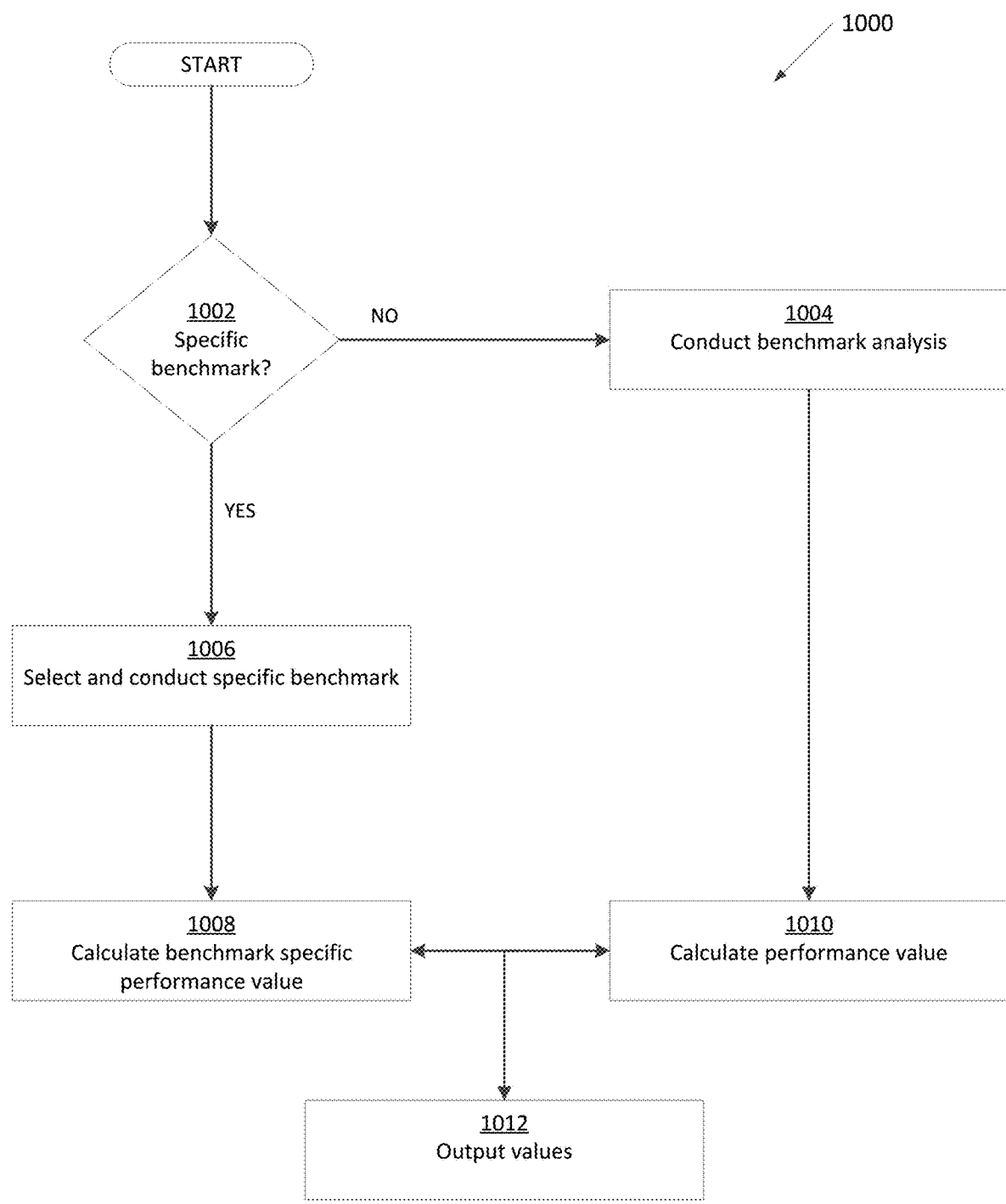
FIG. 10 is a flowchart diagram of an example embodiment for obtaining benchmark data, according to one or more aspects described herein.

FIG. 10 shows flowchart 1000 of an example embodiment for obtaining benchmark data. Flowchart may be exemplary, for example, of processes performed as part of block 606 of flowchart 600 shown in FIG. 6. In particular, FIG. 10 describes one or more processes for obtaining athletic data from benchmarking activities. As such, one or more benchmarking activities may be prescribed to a user in order to determine one or more metrics associated with the user's fitness, strength, or athleticism, among others. Accordingly, in certain examples, a specific benchmarking test may be prescribed for completion by a user. If a specific benchmarking test is to be utilized, the flowchart may proceed from decision block 1002 to block 1006, and a specific benchmarking test may be selected based upon the type of athletic metric test result desired. In one implementation, the specific benchmarking test may be automatically selected based upon the type of coaching plan desired by the user, or may be manually selected by a user from a choice of one or more different types of benchmarking tests. In certain examples, a specific benchmarking test may include, among others, a three minute and a nine minute running test during which the user is tasked with running as far as possible within the given time limit. In another example, a specific benchmarking test may include a three minute all-out running test during which the user is instructed to run as fast as possible for three minutes. It is further contemplated that additional running durations may be utilized during benchmarking testing, and/or that different benchmarking testing methodologies may be utilized, without departing from the scope of these disclosures. In response, a user may complete the prescribed benchmarking test, which may be recorded by one or more sensor devices as previously described herein. One or more performance values may be calculated from the recorded benchmarking test data. As such, the one or more performance values may be specific to a prescribed benchmarking test, and include, among others, a critical velocity associated with the user, and/or an anaerobic work capacity for the user. In one implementation, one or more processes to calculate a benchmark-specific performance value may be executed at block 1008.

In another implementation, if a non-specific benchmarking test is to be utilized, the flowchart may proceed from decision block 1002 to block 1004. As such, a non-specific benchmarking analysis may be executed at block 1004. In one implementation, a user may exercise without benchmarking test constraints (e.g. without a time limit, or without a minimum pace requirement, among others). In another implementation, a benchmarking analysis may utilize test data from a previous athletic activity carried out by the user without benchmarking test constraints. As such, the user may select a previously-recorded athletic activity session for analysis by one or more benchmarking processes. In one example, the benchmark analysis executed at block 1004 may be utilized to calculate one or more performance values, whereby the performance values may not include those performance metrics that may be calculated in response to prescribed and specific benchmarking testing (i.e. may not include critical velocity and/or anaerobic work capacity for a user). As such, one or more performance values calculated from nonspecific benchmarking testing may include, among others, an average speed/average pace of the user across multiple activity sessions. However, it is also contemplated that one or more processes may identify athletic activity within recorded data that may be utilized to calculate performance metrics similar to those calculated from specific benchmarking test data. As such, one or more processes may be utilized to calculate a critical velocity and/or an anaerobic work capacity for a user, from non-specific benchmarking test data. As such, these one or more processes to calculate performance values from non-specific benchmarking test data may be executed at block 1010. Further, the one or more performance values calculated from test data recorded as a result of prescribed benchmarking tests and/or non-specific test data may be outputted at block 1012.

Figure 11:
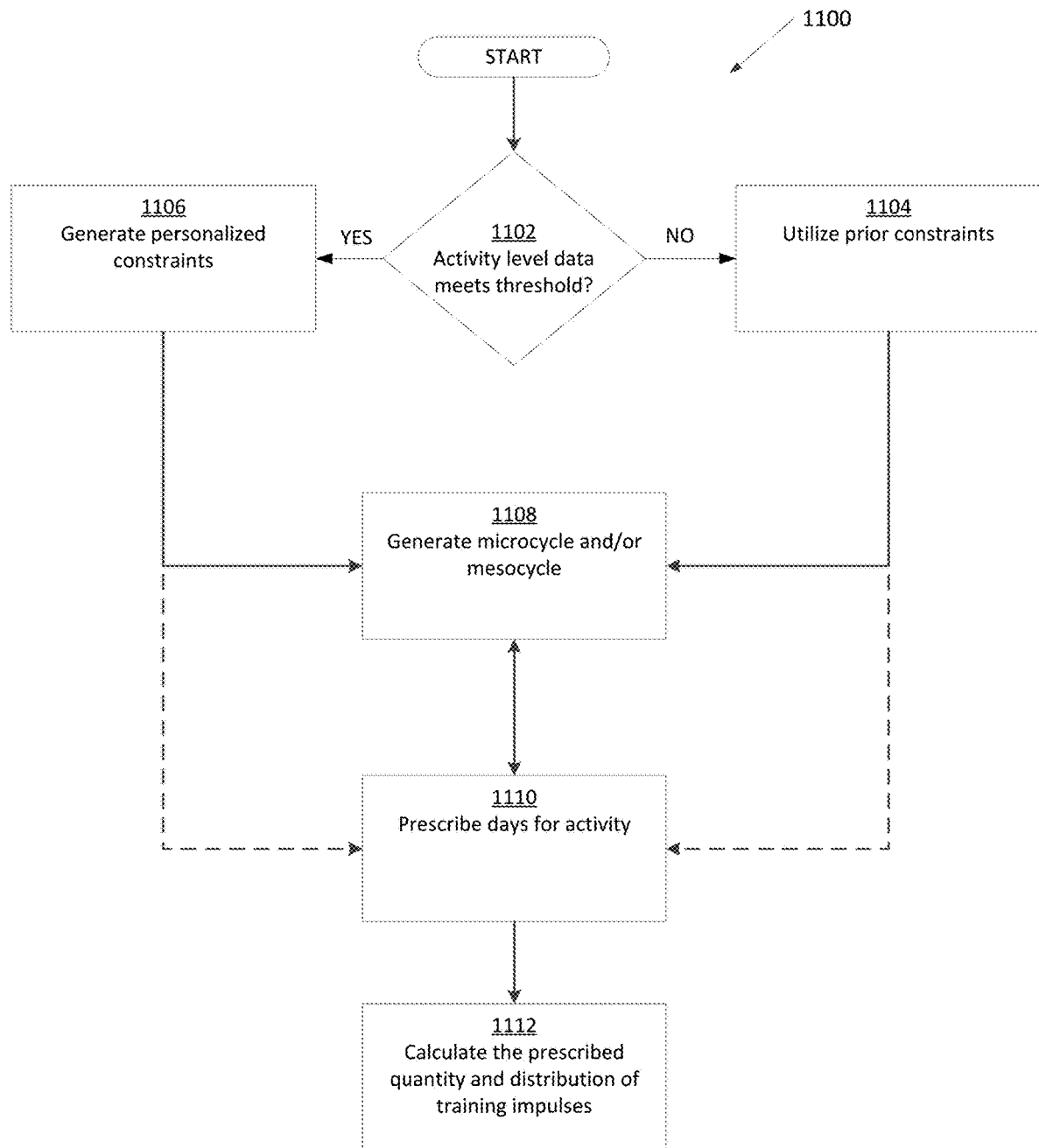
FIG. 11 is a flowchart diagram describes one or more processes that may be utilized to create an athletic prescription for a user, according to one or more aspects described herein.

FIG. 11 is a flowchart diagram describing in further detail one or more processes that may be executed at block 610 of flowchart 600. As such, FIG. 11 describes one or more processes that may be utilized to create an athletic prescription for a user, otherwise referred to as a coaching plan. Decision block 1102 may execute one or more processes to determine whether calculated training impulse data, otherwise referred to as TRIMP data, meets one or more threshold levels associated with the assignment of athletic constants to the user. It is contemplated that any threshold levels may be utilized to determine whether stored TRIMP data may be utilized to generate/assign new athletic constants to a user. For example, one or more new athletic constants may be generated for/assigned to a user based upon stored TRIMP data being available (e.g. calculated at block 704 and/or 608 of flowcharts 700 and 600, respectively) for a previous workout session/day, for two previous workout sessions/days, or for three previous workout sessions/days, among many others. Accordingly, if stored TRIMP data meets or exceeds one or more threshold values, personalized athletic constants may be generated for the user at block 1106. These personalized athletic constants, otherwise referred to as athletic constraints, may be generated based upon a level of activity of the user during a threshold amount of time prior to the current date, which may, in one example, relate to a predicted fitness level of the user. In one implementation, the personalized athletic constants may include, among others, a fitness gain, a fatigue gain, a fitness decay, and a fatigue decay (and may be referred to as K1, K2, T1, T2, respectively). The personalized athletic constants may be retrieved from a stored lookup table that correlates one or more activity levels for the user with stored values for the athletic constants. For example, if a user runs x miles/week he/she may be classified as a beginner, and associated with a first set of athletic constants (K1, K2, T1, T2)_1. If a user runs y miles/week he/she may be classified as an intermediate, and associated with a second set of athletic constants (K1, K2, T1, T2)_2. If a user runs z miles/week he/she may be classified as advanced, and associated with a second set of athletic constants (K1, K2, T1, T2)_3, and the like. In another example, the one or more personalized athletic constants may be calculated based upon the threshold TRIMP data. Accordingly, the athletic constants, K1, K2, T1, T2, may be a function of TRIMP data and benchmark data for a user.

In another implementation, if the stored TRIMP data does not meet one or more thresholds associated with block 1102, the systems and methods described herein may utilize prior athletic constants assigned to the user (e.g. those athletic constants discussed in relation to block 704 of FIG. 7). One or more processes executed to utilized prior-assigned athletic constants may be executed at block 1104. In certain embodiments, the prior constraints are at least partially based upon the experience level of the athlete. For example, in one embodiment an experience level for training, a.k.a. training level may be determined by the current or recent number of hours the athlete works out per week.

Table 1, below, provides one example:

TABLE 1

Example correlation of athletic constraints to training levels

| Hrs per week | Level | K1 | K2 | T1 | T2 |
|---|---|---|---|---|---|
| 0-2 | BEGINNER | 1 | 3 | 20 | 6 |
| 3-6 | INTERMEDIATE | 1 | 3 | 25 | 5 |
| >=7 | ADVANCED | 1 | 2 | 28 | 3 |

In yet another embodiment, an experience level for running, a.k.a. running level, may be determined by the current number of miles the athlete runs per week. Table 2 provides an illustrative example embodiment:

TABLE 2

Example correlation of athletic constraints to different running levels

| Miles per week | Level | K1 | K2 | T1 | T2 |
|---|---|---|---|---|---|
| <10 | BEGINNER | 1 | 2 | 28 | 6 |
| >=10 and <20 | INTERMEDIATE | 1 | 2 | 30 | 5 |
| >=20 | ADVANCED | 1 | 2 | 32 | 4 |

As discussed below, an assigned experience level and/or one or more assigned athletic constraints may be correlated or otherwise associated with assigned periods or lengths of parts of a training or coaching cycle. A coaching plan may be broken down into one or more sub-periods of coaching time. In one implementation, these sub-periods may include microcycles and/or mesocycles. A coaching plan may comprise a training plan, and may be broken down into sub-periods of time referred to as mesocycles. In turn, a mesocycle may be broken down into one or more microcycles. Further, a mesocycle may include a first pattern or selection of training session types/activity types available for prescription to the user. In one specific example, a first mesocycle may be associated with a first group of activity types available for selection by the user. In turn, a second mesocycle may be associated with a second group of activity types, which may be partially or wholly different than the first group of activity types. In one implementation, athletic activities prescribed within a microcycle may be repeated such that a first microcycle may prescribe a first selection of athletic activities, and a second microcycle that follows the first microcycle, and is within a same mesocycle, may prescribe the same first selection of athletic activities. In one example, the second microcycle may prescribe the same selection of athletic activities, but prescribe higher training impulse requirements for the second microcycle. In one implementation, a coaching plan that comprises a running plan may utilize microcycles, but not mesocycles. In one example, a last microcycle in a mesocycle may be referred to as an unload microcycle, and a prescribed training impulse for an unload microcycle may not be increased from an adjacent and previous microcycle. Similarly, the last microcycle in a coaching plan may be referred to as a taper microcycle. As such, a prescribed training load may not be increased during a taper microcycle (in one example, a training impulse of zero may be prescribed during a taper microcycle). In one implementation, first and second mesocycles may have different distributions of paces (e.g. endurance, tempo, threshold, and anaerobic paces), and such that paces may not be excluded from a mesocycle, but may be differently distributed between the first and second mesocycles.

Accordingly, a microcycle length and a mesocycle length may be calculated for the user based upon the athletic constants discussed in relation to blocks 1106 and/or 1108. Initial or otherwise assigned cycle lengths may be directly or indirectly based upon the experience level/constraints. This may be especially useful when an athlete first starts or initiates an adaptive plan. Tables 3 and 4 below show exemplary embodiments in which the example experience level/constraints of Tables 1 and 2 are associated with example microcycle lengths.

Training Level is determined by the current number of hours the athlete works out per week.

| Hrs per week | Level | K1 | K2 | T1 | T2 | Microcycle Length |
|---|---|---|---|---|---|---|
| 0-2 | BEGINNER | 1 | 3 | 20 | 6 | 11 |
| 3-6 | INTERMEDIATE | 1 | 3 | 25 | 5 | 8 |
| >=7 | ADVANCED | 1 | 2 | 28 | 3 | 4 |

Table 3 (above) showing microcycle length associated with at least one of experience level and one or more athletic constraints.

| Miles per week | Level | K1 | K2 | T1 | T2 | Microcycle Length |
|---|---|---|---|---|---|---|
| <10 | BEGINNER | 1 | 2 | 28 | 6 | 7 |
| >=10 and <20 | INTERMEDIATE | 1 | 2 | 30 | 5 | 6 |
| >=20 | ADVANCED | 1 | 2 | 32 | 4 | 5 |

Table 4 (above) showing microcycle length associated with at least one of experience level and one or more athletic constraints.

In one example, the microcycle length may be calculated using the equation:

$$\text{Microcycle length} = (t1 * t2)/(t1-t2) * \ln(k2/k1) \quad \text{(Equation 8)}, \text{where:}$$

t1 (otherwise indicated as T1) may be a fitness decay athletic constant, t2 (otherwise indicated as T2) may be a fatigue decay athletic constant, k1 (otherwise indicated as K1) may be a fitness gain athletic constant, and k2 (otherwise indicated as K2) may be a fatigue gain athletic constant. As such, the athletic constants t1, t2, k1, and k2 may be personalized constants generated at block 1106, or may be those prior-assigned athletic constants discussed in relation to block 1104. Additionally, it is contemplated that the microcycle length calculated from Equation 8 may be a whole number of days, and as such, the result of Equation. 8 may be rounded. In one example, the result of Equation 8 may be rounded up. Further, it is contemplated, in one implementation, the microcycle length may be limited to between 4 and 14 days (inclusive). In one specific example, a maximum microcycle length may be equal to 10 days. However, it is contemplated that different microcycle length limits may be utilized, without departing from the scope of these disclosures.

In one implementation, a mesocycle length may be calculated using the equation:

$$\text{Greatest influence value} = ((\ln((k2/k1) * (t1/t2)) * t1 * t2/(t1-t2)) + 1) \quad \text{(Equation. 9)},$$

where:

t1 (otherwise indicated as T1) may be a fitness decay athletic constant, t2 (otherwise indicated as T2) may be a fatigue decay athletic constant, k1 (otherwise indicated as K1) may be a fitness gain athletic constant, and k2 (otherwise indicated as K2) may be a fatigue gain athletic constant. As such, the athletic constants t1, t2, k1, and k2 may be personalized constants, such as generated at one or more processes in this disclosure, or may be those prior-assigned athletic constants discussed above. In one example, Equation 9 may be rounded up. However, it is contemplated that Equation 9 be utilized without rounding, or with rounding down, without departing from the scope of these disclosures. Regardless of how a mesocycle length is calculated, certain embodiments may set a minimum duration for the mesocycle. In one embodiment, a mesocycle length may be about one month, in yet another embodiment a mesocycle is at least 30 days.

Using a calculated greatest influence value, the mesocycle length may be calculated using an influence curve for an athlete that plots a net influence per unit training stress on performance on each day before a day of a goal performance (e.g. a race day). An example influence curve is shown in FIG. 15A. In particular, the mesocycle length may be determined using a net influence per unit training stress (y-axis value) that is equal to a portion (e.g., half) of a second net influence per unit training stress value, with this second value corresponding to the greatest influence value calculated from another process. In one embodiment, Equation 9 may be utilized. Accordingly, when plotted, the second net influence per unit training stress value will correspond to a number of days prior to a goal performance day, and this number of days may be set equal to the mesocycle length. Further, these one or more processes to calculate a microcycle and a mesocycle length may be executed at block 1108.

One or more processes may be utilized to determine specific days on which a user is prescribed athletic activities to be completed in order to progress through a coaching plan that may be utilized for training towards a running goal or another goal type (e.g. a cross-training goal, strength goal, among many others). In one example, these one or more processes for determining specific days on which a user is prescribed athletic activities completed may be executed at block 1110, and may utilize the following methodology:

A weekly workout ratio may be calculated using a user input entered manually (e.g. at block 602 of FIG. 6). In particular, the weekly workout ratio may be calculated as being equal to a number of days per week that the user is willing to work out divided by seven (i.e. the number of days per week):

$$\text{Weekly workout ratio} = (\text{number of days user specified he/she wants to work out per week})/7. \quad \text{(Equation 10)}.$$

In one example, one or more processes may be utilized to prescribe workouts between a current date and a goal performance date, which may be a date manually-provided by the user. As such, the number of days on which a workout is to be prescribed to the user may be calculated as being equal to:

$$\text{Number of workouts to prescribe} = (\text{weekly workout ratio}) * (\text{days left until goal date}). \quad \text{(Equation 11)}.$$

The methodology used to prescribe athletic activities to be completed by the user may consider a number of past workout days. In one example, a relevantDayInPast variable may be initialized as being equal to the minimum of a set of days, e.g. four days, or a number of days since a coaching plan was started by the user. Additionally, for each of the workout days considered in the past, the systems and methods described herein may search for and analyze a number of workouts completed. The number of workouts completed may be counted as variable relevant WorkoutsInPast. Further, a target workout ratio may be defined as:

$$\text{Target workout ratio} = ((\text{number of workouts to prescribe}) + (\text{relevantWorkoutsInPast}))/((\text{days left until goal date}) + (\text{relevantDayInPast})). \quad \text{(Equation 12)}$$

In one example, the systems and methods utilized to determine specific days on which a user is prescribed athletic activities to be completed in order to progress through a coaching plan may utilize a currentWorkouts variable, initialized equal to the relevantWorkoutsInPast variable. Additionally, a currentTotalDays variable may be initialized as being equal to the relevantDayInPast variable.

Further, for each day left in the coaching plan until a goal date, the systems and methods described herein may execute one or more processes to:

Utilize an addWorkoutRatio, with the $$\text{addWorkoutRatio} = (\text{currentWorkouts}+1)/(\text{currentTotalDays}+1) \quad \text{(Equation 13)}.$$

Additionally, a restRatio may be utilized, with the $$\text{restRatio} = \text{currentWorkouts}/(\text{currentTotalDays}+1) \quad \text{(Equation 14)}.$$

Further, the systems and methods described herein may execute one or more processes for each day left in the coaching plan until a goal date that calculates an absolute value of differences between ratios the day by first calculating an absolute values of $$(\text{Target workout ratio} - \text{addWorkoutRatio}) \quad \text{(Equation 15) and}$$

$$(\text{Target workout ratio} - \text{restRatio}) \quad \text{(Equation 16)}.$$

If the result of Equation 15 is less than or equal to Equation 16, the day in question may have a workout prescribed for it, otherwise the day in question may be designated a rest day.

In one implementation, the one or more processes that may be utilized to determine specific days on which a user is prescribed athletic activities to be completed in order to progress through a coaching plan (e.g. utilizing Equations 10, 11, 12, 13, 14, 15, and/or 16) may be executed at block 1110.

It is also contemplated that one or more processes may be utilized to calculate an amount of athletic activity (e.g. a training impulse, TRIMP, value) to be completed by the user for each day at which an athletic activity is prescribed, as determined at block 1110. Further, a distribution of the prescribed amounts of athletic activity may be determined. This calculation of the various athletic activities to be carried out on each of the days on which an athletic activity is to be undertaken by the user, as well as the calculation of the distribution of the prescribed amounts of athletic activity, may be executed at block 1112. One or more example processes that may be conducted as part of block 1112 are described in further detail in relation to FIG. 12.

Figure 12:
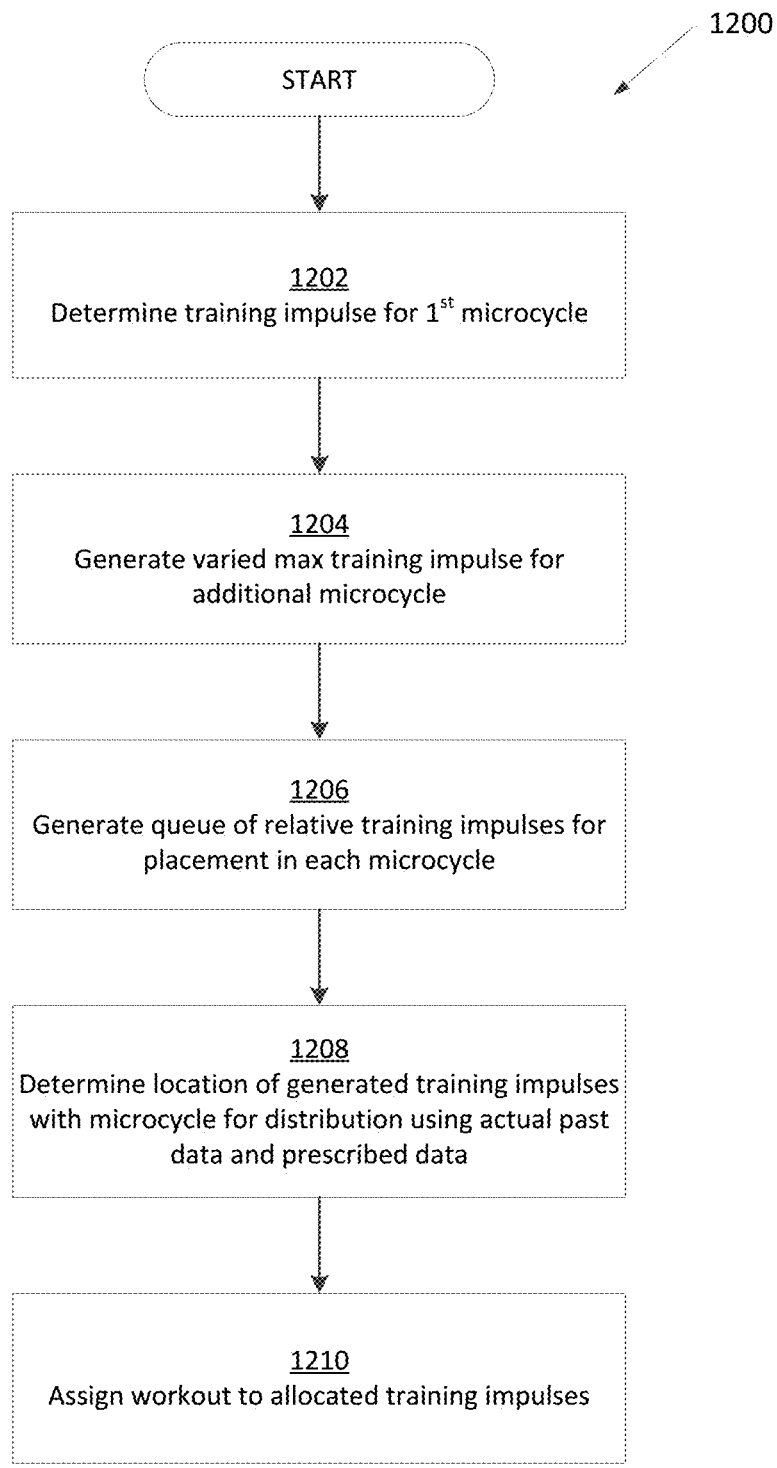
FIG. 12 is a flowchart diagram describing in further detail one or more example processes that may be executed to calculate a prescribed quantity and distribution of training impulses, according to one or more aspects described herein.

FIG. 12 is a flowchart diagram describing in further detail one or more example processes that may be executed at block 1112 from FIG. 11. In one implementation, the microcycle length calculated at block 1108 may be utilized to subdivide a duration of time between a current date and a goal date into one or more microcycles. In one implementation, each microcycle will have a maximum training impulse associated therewith. A first microcycle may be defined as a number of days spanning a number of days into the future from a current day equal to the previously-calculated microcycle length. The maximum training impulse for the first microcycle may be retrieved from a lookup table stored in memory. In one example, the lookup table may map a number of miles run by an athlete per week with a starting maximum training impulse value. However, it is also contemplated that the lookup table may map a number of hours spent training per week with a starting maximum training impulse value, among others. In one implementation, the maximum training impulse for the first microcycle may be selected at block 1202.

Accordingly, as a user progresses through multiple microcycles of a coaching plan, the maximum training impulses for a given microcycle may be automatically increased. In one example, a maximum training impulse for a given microcycle will be increased by a certain percentage, such as 8%, from the immediately-preceding microcycle. However, it is contemplated that any percentage increase may be utilized, or a variable increase value may be utilized, without departing from the scope of these disclosures. In another implementation, a maximum training impulse for a given microcycle may be increased by a fixed amount, rather than a fixed percentage. In particular, the maximum training impulse increase may be increased by a maximum fixed amount stored in a lookup table, and based upon a training goal associated with the user. For example, for a user training to compete in a marathon, a maximum training impulse increase may be specified as x miles/week (e.g. a maximum increase of 1 mile/week). In another example for a user training to complete in a 5 k or a 10 k race, a maximum training impulse increase may be specified as y miles/week (e.g. a maximum increase of 0.5 miles/week). Further the maximum training impulse increase specified in units of, in one example, miles/week may be converted into a maximum training impulse per microcycle using the formula:

$$\text{Maximum increase per microcycle}/\text{Microcycle length} = \text{Maximum training impulse increase per week}/7. \quad \text{(Equation 17)}$$

In one implementation, a maximum training impulse value for each microcycle may be sequentially calculated based upon a maximum training impulse for and immediately-proceeding microcycle, and may be executed by one or more processes associated with block 1204.

As previously discussed, each microcycle of a given coaching plan may comprise a prescribed maximum training impulse. Additionally, other days within a given microcycle may prescribe lower training impulse workouts/athletic activities. Accordingly, the systems and methods described herein may calculate a queue of training impulse values for each microcycle, based upon the maximum training impulses calculated. In one example, the queue of training impulses for a given microcycle may start with the calculated maximum training impulse. The second training impulse may be calculated as being equal to a percentage or fraction of the maximum training impulse for the microcycle, such as for example ⅔*(max training impulse for the microcycle). Further, the third and subsequent training impulses may be calculated as being equal to another fraction or percentage. In one embodiment, it may be ⅓*(max training impulse for the microcycle). It is contemplated, however, that any multipliers may be utilized to construct a queue of training impulses based upon a maximum training impulse for a given microcycle, without departing from the scope of these disclosures. In certain implementations, the maximum training impulse prescribed for a microcycle is not increased as a user progresses from a given microcycle into an unload microcycle/period or a tapering microcycle/period. In another implementation, the maximum training impulse prescribed for a micro cycle is increased as a user progresses from a first microcycle preceding an unload microcycle into a second microcycle proceeding the unload microcycle. For example, for 4 microcycles, the third being an unload microcycle, the increasing training impulses may be of the form of: x, x+2, x (i.e. unload microcycle), x+4 (i.e. the microcycle training impulse after the unload microcycle increases linearly from the last non-unload microcycle).

In one example, an unload period may be defined at a mesocycle boundary (i.e. as a user transitions from one mesocycle into another). In one example, a tapering period may be the last microcycle before a goal date (i.e. before a race day, among others). Accordingly, one or more processes to calculate a queue of training impulses for each microcycle may be executed at block 1206. In certain embodiments, maximum TRIMP values may progress even during one or more taper and/or unload microcycles.

In one implementation, a distribution of prescribed training impulses within a microcycle may be calculated in order to distribute the generated queue of training impulses, as described in relation to block 1206. Accordingly, one or more processes may be executed at block 1208 in order to determine a distribution of those calculated training impulses (calculated at block 1206) among those days within a microcycle for which athletic activities are to be prescribed (e.g. calculated at block 1110 of FIG. 11). In one example, the one or more processes executed at block 1208 may determine a best distribution of training impulses by considering all possible permutations of those possible distributions of training impulses across those days within a microcycle on which an athletic activity is to be prescribed. In another implementation, the one or more processes executed at block 1208 may determine a distribution of training impulses by considering a reduced number of permutations of possible distributions of training impulses since, as described in relation to block 1206, the third and subsequent training impulses may be calculated as being equal to $\frac{1}{3}*$(max training impulse for the microcycle) (i.e. there is repetition of training impulse values). Accordingly, it will be understood that for n days within a microcycle that are to be populated with training impulses from the calculated training impulse queue from block 1206, there will be there will be $nPn/(n-2)!$ permutations of training impulses to be considered by the one or more processes executed at block 1208 (i.e. there are n–2 repetitions of training impulse values corresponding to the third and subsequent training impulses up to the n values used to fill the n days of the microcycle that are to be populated with training impulses from the training impulse queue calculated at block 1206.

A best permutation of training impulses across the days of a microcycle may be determined by calculating rolling averages for each permutation of interest (i.e. taking into account the n–2 repetitions of training impulse values for n days to be populated in a microcycle). Accordingly, in order to calculate a rolling average for each permutation of interest, a rolling average size may be calculated as:

$$\text{Rolling average size} = \text{microcycle length}/2 \qquad \text{(Equation 18)}.$$

Further, Equation 18 may, in one implementation, be rounded up. A number of past days (prior to the first day of a microcycle) to be considered may be defined as:

$$\text{Past days} = \text{rolling average size} - 1 \qquad \text{(Equation 19)}.$$

Accordingly, for each permutation of training impulses across the days of a microcycle, one or more processes may be executed to calculate an average of every possible set of three training impulses associated with consecutive days of the microcycle. Further the averages of every possible set of three training impulses may include the number of Past days calculated from Equation 19 above. These one or more processes will generate multiple average values, each averaging training impulse values for three consecutive days (in one implementation, a training impulse value from one or more of these consecutive days may equal zero). In one example, M average values may be calculated. Further, within the M average values there will be a numerically largest and a numerically smallest value. For each permutation of training impulses, a numerical difference between the numerically largest and the numerically smallest number within the M average values may be calculated. The difference may be referred to a permutation score. Accordingly, in one example, the permutation of training impulses with the lowest permutation score may be selected as the best distribution of prescribed training impulses within a microcycle.

In one example, block 1210 may be utilized to assign a work out to the distributed training impulse values across the days during which an athletic activity is to be prescribed to the user within a microcycle of a coaching plan. The one or more processes associated with block 1210 are described in further detail in relation to FIG. 14.

Figure 13A:
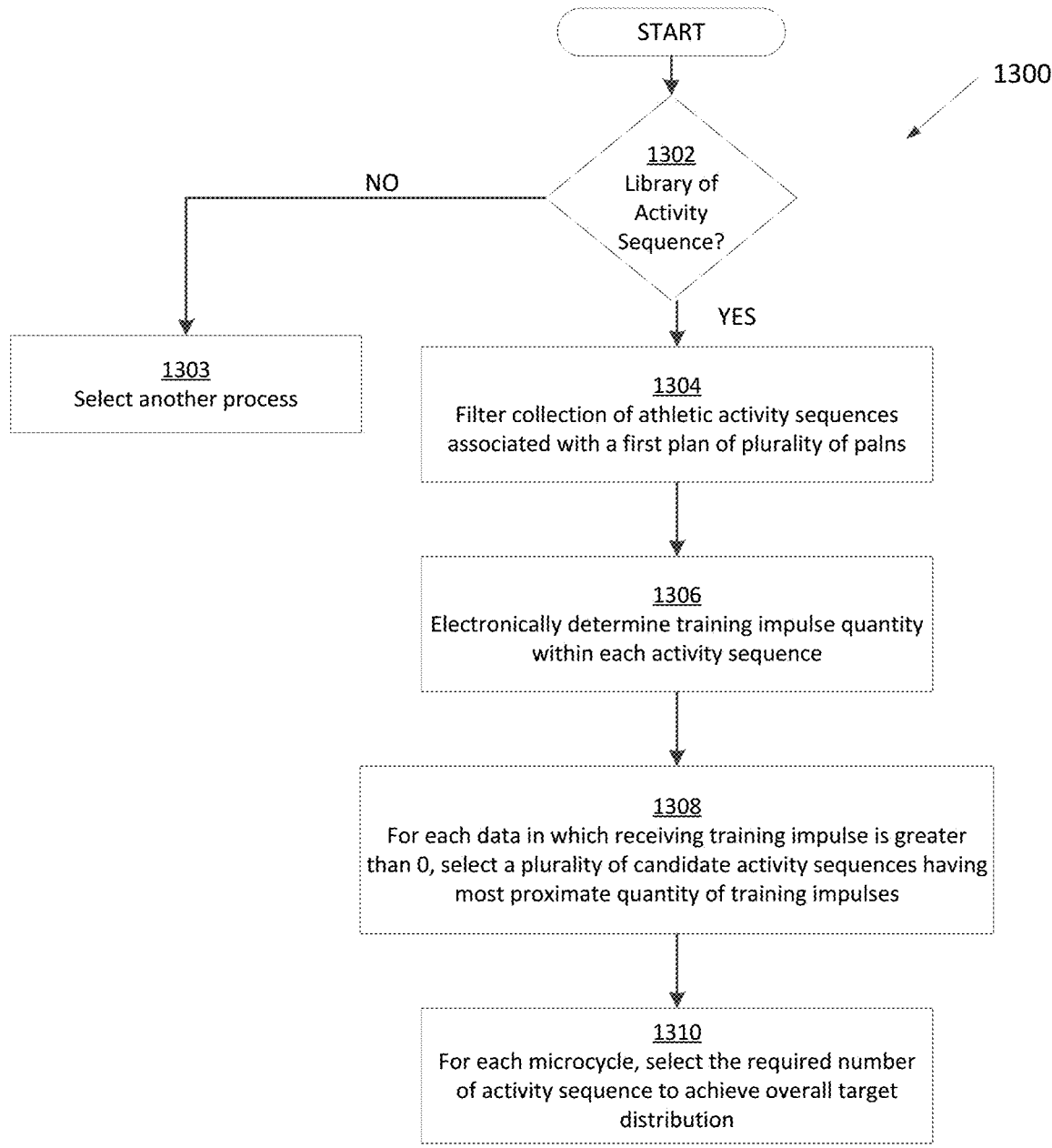
FIG. 13A is a flowchart diagram describing one or more processes utilized to select an activity distribution corresponding to one or more prescribed training impulses of a running coaching plan, according to one or more aspects described herein.

FIG. 13A is a flowchart diagram describing one or more processes utilized to select an activity (running activities) distribution, otherwise referred to as an activity sequence, corresponding to one or more prescribed training impulses of a running coaching plan. Accordingly, decision block 1302 may represent one or more processes executed to determine if there is a library of activity sequences stored in memory from which one or more activity sequences can be selected.

If, in response to decision 1302 there is not a library (or there is not an adequate library) of activity sequences available for searching, the flowchart may proceed to block 1303 to generate a library.

If, in response to decision 1302 there is a library of activity sequences available for searching, the flowchart may proceed to block 1304 by one or more processes may be executed to filter the collection of athletic activity sequences. In one implementation, one or more filtering processes may exclude activity sequences that are unrelated to an activity type associated with a coaching plan being sought by the user. For example, the one or more filtering processes may exclude activity sequences that are unrelated to running when selecting activity sequences for a running coaching plan. It is contemplated that additional filtering parameters may include, among others, user bibliographic data (e.g. age, sex, height, weight), equipment available to the user, and/or a general work out type preferred by the user.

In one example, one or more processes may be executed to determine a training impulse quantity associated with an activity sequence within a library/database of activity sequences. Accordingly, in one implementation, the training impulse quantities may be stored within a same database as descriptors of one or more potential activity sequences. In another example, training impulse quantities associated with each activity sequence within a database of potential activity sequences may be calculated based upon descriptors of the one or more potential activity sequences, and utilizing bibliographic data of the user intending to perform one or more of the activity sequences. For example, a training impulse quantity, or energy expenditure value, associated with an activity sequence may be calculated based upon a weight of a user if the activity sequence comprises one or more body-weight exercises. These one or more processes to determine one or more training impulse quantities associated with an activity sequence within a database of sequences may be executed at block 1306.

In another embodiment, instead of selecting a certain number of workouts within a threshold proximity to the desired training impulse, a selection may be a function of a size of a filtered library. For example, if the filtered library is equal to or greater than a first value (e.g., 5), but less than or equal to a second value (e.g., 10) then a first quantity of "closest" workouts may be selected (e.g., as little as 1), yet if the filtered library contains more than (or is equal to) the second value, then a second quantity of "closest" workouts may be selected" (e.g. 2 workouts may be selected). The equation below shows one non-limiting illustrative example of logic that may be utilized:

If filtered library size is greater than or equal to 5;
closest workouts to select=1
Else if filtered size is greater than or equal to 10;
closest workouts to select=2
Else
closest workouts to select=(7, round (filtered library size/7))

In certain embodiments, the selection may comprise looking to factors, such as the percentage or threshold level of the prescribed TRIMPS within possible workouts that relate to focus areas, such as for example: strength, endurance and mobility. Yet, other more precise aspects may be considered, such as one or more of: Upper Body Strength; Lower Body Strength; Upper Body Mobility; Lower Body Mobility; Agility; Single Leg Stability; Core Stability; Endurance; and/or Quickness.

One or more processes may iterate through each microcycle within a running coaching plan and each day within each microcycle. Accordingly, for each day within a microcycle that has a prescribed training impulse value greater than zero, one or more processes may select one or more candidate activity sequences, from the activity sequence database, having training impulse values proximate to a training impulse quantity prescribed for said day. In one implementation, seven candidate activity sequences may be identified within an activity sequence database as having training impulse values proximate to a prescribed training impulse value. However, it is contemplated that any number of candidate activity sequences may be identified, without departing from the scope of these disclosures. These one or more processes may be executed at, in one example, block 1308.

Certain embodiments may consider a focus or plan the user selected or otherwise is categorized in and/or their actual performance. For example, if a user selects a plan that intends to run a race of a specified distance, then running activities that are designed to progress the distance goal may be considered. The consideration may take into account the TRIM" count for such activities. For example, a prescribed activity may be 25% directed towards improving Endurance, thus that TRIM" count (e.g., 100 TRIMPS), may be multiplied by 0.25% to note that 25 TRIMPS may be quantified towards the plan goal of endurance improvement. Further, the user's actual performance may be considered. For example, if the user is the same plan as above (50% endurance and 50% mobility), however, is showing a need for more endurance or stability, then those may be increased by a factor. Thus, possible selections may be considered based upon their overall make up with respect to one or more individual focus areas or goals, which may be with respect to the athlete's desires, experience level, and/or actual performance.

In turn, for each day of each microcycle, one or more activity sequences may be automatically selected that will achieve a target/prescribed training impulse value, based on training impulse values mapped to activity sequences, and stored within an activity sequence database.

Distributions may be defined in terms of pace buckets, which may be expressed as percentages of a user's critical velocity. In one example, pace buckets may be defined as follows:

Endurance: <85% CV, Tempo: 85-95% CV, Threshold: 95-105% CV, VO2 Max: 105-120% CV, Anaerobic Capacity: >120% CV Prescribed or completed runs may be broken down into a vector of these pace buckets. For example, if a user completed a 4-mile run at 90% of their critical velocity, that run would be broken down as follows:

Endurance—0, Tempo: 100, Threshold: 0, VO2 Max: 0, Anaerobic Capacity: 0

In the example above, the vector of pace buckets is arrived at because the entirety of the user's run was spent in the "tempo" pace bucket. A single run will be entirely in one pace bucket if the entire run is at a consistent pace. However, a run may also span multiple buckets if the pace varies during the run.

Target distributions are dictated by the mesocycle the user is in, as well as their level (BEGINNER, INTERMEDIATE, or ADVANCED) and their goal (5K, 10K, etc.). These are stored in a lookup table in memory. So, for a given combination, for example, a beginning user in a 5 k plan in their 2nd mesocycle, they will have a fixed target distribution, like the following:

Target Distribution: Endurance—50, Tempo—20, Threshold—10, VO2 Max—10, AC—10

This target distribution is the balance of workouts that will result in 50% of the training load being spent in the endurance bucket, 20% of the training load in tempo pace bucket, etc. Systems and methods may aim to result in the closest overall target distribution per microcycle. Accordingly, it is further contemplated that methodology for selection of a combination of activity sequences may be employed, e.g. at block 1310. This methodology may consider one or more permutations of candidate athletic sequences, from the one of more candidate activity sequences. In certain implementations, a permutation score may be calculated for one or more permutations of candidate athletic sequences, and a permutation with a best score may be selected. This permutation score may or may not be a simple Euclidean distance between the permutation distribution and the target distribution, or some other distance heuristic. The permutation that has a score that is deemed closest to the target distribution will be chosen for each microcycle.

In certain embodiments, custom drills may be created. For example, if the known TRIMP value for the day is known, and the user wants to improve upper body strength, selecting upper body routines associated with TRIMP values (which may even be calculated from past activity the same athlete has performed) may be scaled by setting a quantity of reps and sets In one specific example, a coaching plan may be prevented from prescribing two long runs in a row, and such that a second of two long runs will be changed to a recovery run, among others.

In one implementation, a running coaching plan may prescribe a fixed running plan for a user for a first two weeks of the plan. As such every user within a same level (same range of no. of miles run per week) and same number of days available to workout per week will be prescribed a same running plan for the first two weeks. An example of the type of plan prescribed for the first two weeks is shown in the tables of FIG. 13B.

Figure 14:
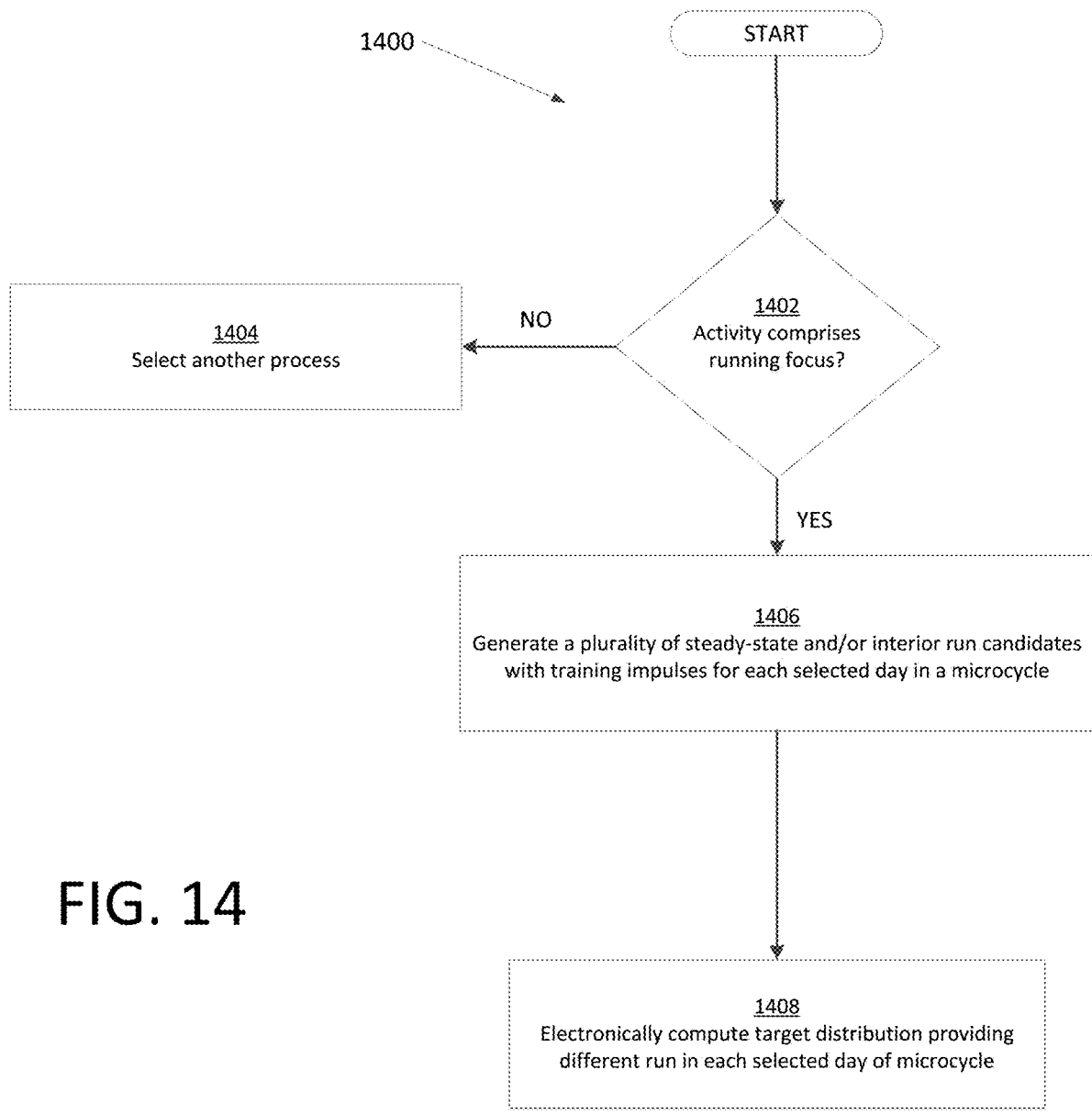
FIG. 14 is a flowchart diagram describing one or more processes utilized to create one or more athletic activities corresponding to one or more prescribed training impulses of a running coaching plan, according to one or more aspects described herein.

FIG. 14 is a flowchart diagram describing one or more processes utilized to create one or more athletic activities corresponding to one or more prescribed training impulses of a running coaching plan. Decision block 1402 may be utilized to determine if a prescribed training impulse has a running focus, or is primarily related to a running coaching plan. Accordingly, if a prescribed training impulse is not associated with a running focused, the flowchart may proceed to block 1404, and one or more processes may be executed to select another process type. If, however, a prescribed training impulse is associated with a running focus, the flowchart may proceed to block 1406, and one or more processes may generate a plurality of steady-state and/or interval run candidates having associated training impulse values corresponding to prescribed training impulses for each day in a microcycle of a running coaching plan. In particular, in order to generate one or more steady-state runs corresponding to a prescribed training impulse, one or more processes may calculate a steadyStatePace variable that is based on a calculated critical velocity (e.g. as calculated in one or more of blocks 820-824 of flowchart 800, for example). In one specific example, the steadyStatePace may be a percentage of the critical velocity. In one embodiment, it may be approximately 0.845*(critical velocity). However, it is contemplated that any multipliers may be utilized, without departing from the scope of these disclosures. In certain examples, three run options may be generated corresponding to three paces, which may be referred to as tempo, threshold and recovery runs.

The steadyStatePace may be considered as a fraction a user's critical velocity (i.e. a relative intensity variable). Further, the prescribed training impulse (TRIMP_prescribed) may be utilized to calculate a desiredDuration variable (duration of run at the steadyStatePace). It may be conducted using the following formula:

desiredDuration=(TRIMP_prescribed)/(relative intensity)   (Equation 20)

Accordingly, the systems and methods described herein may prescribe one or more steady-state runs for a duration equal to the desiredDuration variable, and at a pace equal to the steadyStatePace.

In another example, the systems and methods described herein may prescribe one or more interval runs. In one example, the variables associated with an interval run may include, among others, a number of repetitions (reps), a distance, a pace, and a rest duration. In one implementation, the distance of an interval run may be limited to certain predefined distance options. Accordingly, the set of interval distances from which one or more interval runs may be generated may include distances of 200 m, 400 m, 800 m, 1000 m, 1200 m, and 1600 m. However, it is contemplated that any distances may be utilized, without departing from the scope of these disclosures. In one embodiment, a pace of an interval run to be generated may be selected from a set of acceptable pace values. In one implementation, the set of acceptable paces may be defined relative to a user's critical velocity (CV), and may include paces of set as percentages of the CV. In one embodiment, it may be, for example: 93%*CV, 98%*CV, 103%*CV . . . , 150%*CV. However, it is contemplated that any paces may be utilized, without departing from the scope of these disclosures. With regard to the number of repetitions, in one example, a set of possible repetitions utilized to generate one or more interval runs may be limited to 2-17 repetitions. However, it is contemplated that any number of repetitions may be utilized, without departing from the scope of these disclosures. Similarly, an acceptable rest duration in between repetitions may, in one example, be limited to a duration between 30 seconds and five minutes. However, it is contemplated that any rest duration may be utilized, without departing from the scope of these disclosures.

In one implementation, one or more processes may be executed to generate a list of all possible interval runs that have a training impulse value equal to a prescribed training impulse for a given day of a running coaching plan for a user, and generated based on those limits discussed in relation to the number of repetitions, the interval distance, the acceptable paces, and the acceptable rest durations. In one example, a best interval run may be selected based upon one or more sensor types. In another example, multiple interval runs may be presented to a user, and the user may select a desired interval run type. In one specific example, an interval run that is generated/filtered out of possible run permutations may be based upon an amount of anaerobic work capacity depleted during the interval run. Accordingly, in one example, an acceptable interval run may deplete a user's anaerobic work capacity to between 10% and 50% of the user's total anaerobic work capacity store. In other implementations, it is contemplated that this anaerobic work capacity depletion may result in a user's anaerobic work capacity being depleted to less than 10%, or greater than 50%, without departing from the scope of these disclosures.

In one example, a plurality of steady-state and/or interval runs may be generated for each day during a running coaching plan that is associated with a prescribed training impulse value greater than zero, and utilizing the processes described above, e.g. at block 1406. Additionally, one or more steady-state and/or interval running routes may be recommended to the user based upon, among others, a detected geographic location of the user, a prescribed training impulse value associated with a given run type, or recommendations of running routes from social media links among others. These recommended running routes may be automatically selected from a database, and presented to a user in combination with one or more specific, prescribed run types. As such, the user may be provided one or more maps, as well as other route information (e.g. distance information, terrain classification, reviews from other runners, among others) outlining potential running routes compatible with a prescribed running plan for a given day, or for multiple days within a coaching plan.

Accordingly, for each day that prescribes a training impulse to the user, a single steady-state run, a single interval run, multiple steady-state runs, multiple interval runs, or combinations thereof may be generated and prescribed to the user, e.g. at block 1408. As such, the user may, when given multiple run options, select an option that appeals to him/her on a given day. In certain examples, further limits may be utilized with a running coaching plan, without departing from the scope of these disclosures. For example, for a maximum training impulse day within a microcycle, only a steady-state run may be generated for completion by the user. In another example, for the second to highest training impulse day within a microcycle, only an interval run may be generated for completion by the user, among others.

FIG. 15A schematically depicts an influence curve for a given user. In particular, influence curve 1502 plots a net influence per unit training stress on performance (on the y-axis 1504) versus a number of days until a goal performance date (on the x-axis 1506). As such, the influence curve 1502 may describe a net benefit that a training stress will have on a user's performance on the goal performance date for a prescribed unit training stress at any given time during a coaching plan prior to the goal performance date. In one implementation, the influence curve 1502 may be plotted based upon one or more athletic constants generated for a given user. These athletic constants may include, among others, a fitness gain, a fatigue gain, a fitness decay, and a fatigue decay, as discussed in relation to FIG. 11 and/or block 704 of FIG. 7. It can be observed that as the user progresses through a coaching plan, the positive influence that an amount of training will have on the goal performance date gets progressively higher, and reaches a peak, t_g, otherwise referred to as a point of greatest influence, corresponding to net influence value 1508. This greatest influence value may correspond to a value calculated by, in one example, Equation 9. Further, this point of greatest influence may be the point after which there will be a progressively decreasing positive influence on performance on the goal performance day per unit of training stress prescribed to the user based upon the recovery time needed by the user following completion of a unit training stress. Influence value 1510 may, in one example be equal to half of 1508 (although it is contemplated that other fractions of influence value 1508 may be utilized, without departing from the scope of these disclosures). Accordingly, influence value 1510 may be projected onto curve 1502 in order to find the length 1512 which may be utilized as the mesocycle length specific to the user associated with curve 1502.

It may also be observed that the curve 1502 crosses the x-axis 1506 as the user gets closer to the goal date. This crossover point corresponds to the day after which any additional training stress undertaken by the user will have a detrimental impact on the user's performance on the goal date. The period after this crossover point may be referred to as a tapering period within a coaching plan for the user. Accordingly, the length of time between the crossover point and a goal date, indicated as length 1514, may be set equal to the microcycle length for the user. This length 1514 may correspond to the result of Equation 8, discussed in relation to FIG. 11.

In one embodiment, the training influence equation below may be used to calculate a net unit training influence for a given day.

> Training influence in a given day=$K1*e^{(-(days\ until\ completion)/T1)} - K2^{(-(days\ until\ completion)/T2)}$, where the constants include: fitness gain $K1$, a fatigue gain $K2$, a fitness decay $T1$, and a fatigue decay $T2$ FIG. 15B depicts empirical data used to derive equations for calculation of a critical velocity of the user when running, according to one or more aspects described herein. In particular, graph 1530 plots fraction of critical velocity [dimensionless] (y-axis) versus time [seconds] (x-axis) for multiple different data points (each data point may be a different test run). A regression curve is fitted to the depicted data points, with the equation of the curve calculated as: $y=1.8677*x^{(-0.082)}$, and an $R^2$ value of 0.6816. Graph 1532 plots fraction of critical velocity [dimensionless] (y-axis) versus distance [meters] (x-axis) for multiple different data points (similar to graph 1530, each data point may be a different test run). A regression curve is fitted to the depicted data points, with the equation of the curve calculated as: $y=2.2398*x^{(-0.09)}$, and an $R^2$ value of 0.6779.

FIG. 15C depicts empirical data used to derive equations for calculation of a critical velocity of the user when cycling, according to one or more aspects described herein. In particular, graph 1534 plots fraction of critical velocity [dimensionless] (y-axis) versus time [seconds] (x-axis) for multiple different data points (each data point may be a different test cycle). A regression curve is fitted to the depicted data points, with the equation of the curve calculated as: $y=1.9199*x^{(-0.088)}$, and an $R^2$ value of 0.8053. Graph 1536 plots fraction of critical velocity [dimensionless] (y-axis) versus distance [meters] (x-axis) for multiple different data points (similar to graph 1534, each data point may be a different test run). A regression curve is fitted to the depicted data points, with the equation of the curve calculated as: $y=3.0889*x^{(-0.086)}$, and an $R^2$ value of 0.6769.

Figure 16:
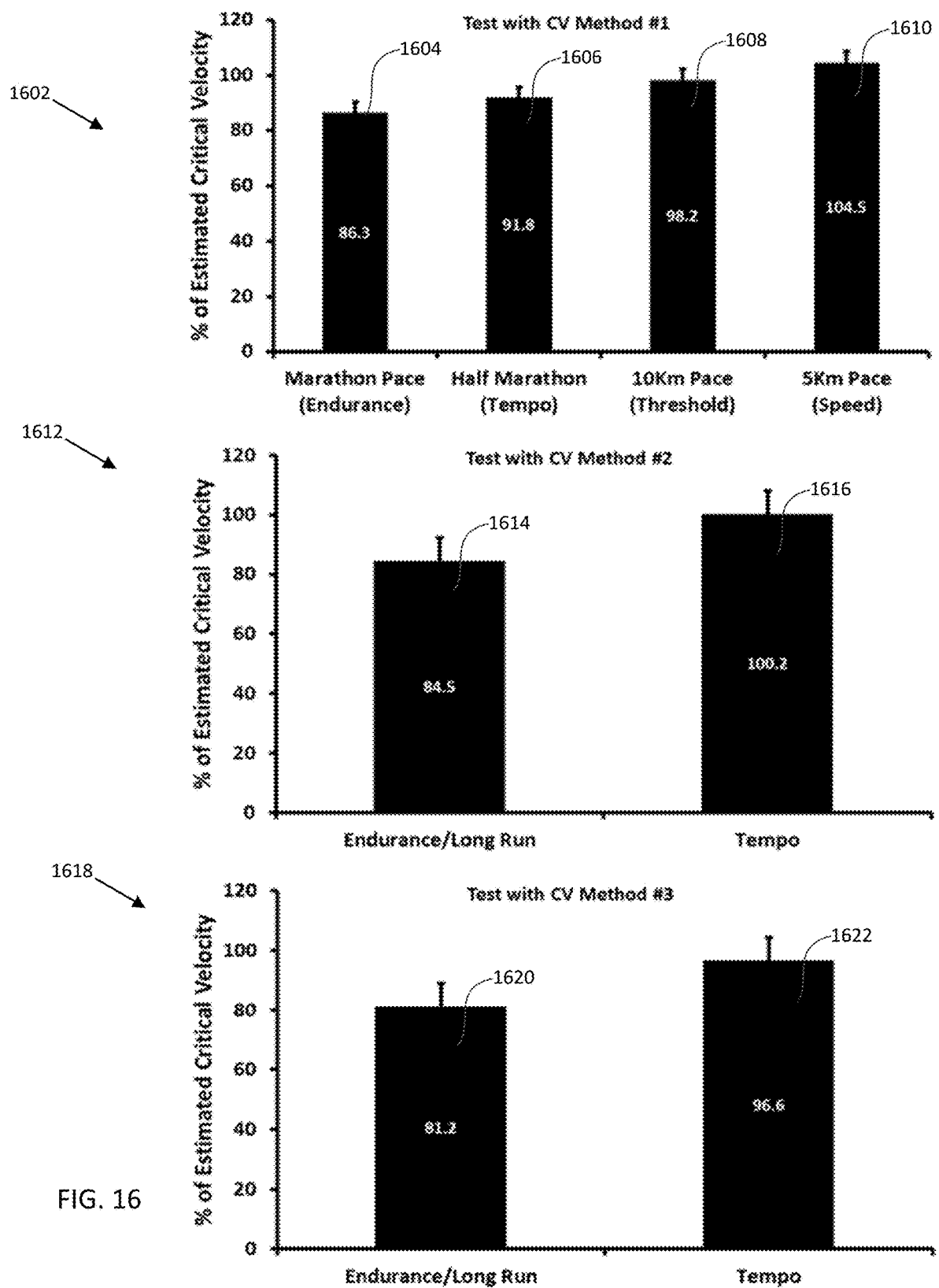
FIG. 16 depicts graphs of test data used to estimate critical velocity of a user based upon a type of run undertaken by the user, according to one or more aspects described herein.

FIG. 16 depicts graphs of test data used to estimate critical velocity of a user based upon a type of run undertaken by the user. In particular, graph 1602 plots percentage of estimated critical velocity of a user (y-axis) for four different run types, and estimated using a first calculation methodology for calculating critical velocity. In particular, the test data indicates that a user's pace over the course of a marathon run/endurance run (1604) will equal approximately 86.3% of the critical velocity for the user. Similarly, the user's pace for a half marathon/tempo run (1606) will equal approximately 91.8% of the critical velocity for the user. Additionally, the user's pace for a 10 km run (threshold run) (1608) will equal approximately 98.2% of the user's critical velocity. Further, a user's pace for a 5 km run (speed run) will equal approximately 104.5% of the user's critical velocity.

Graph 1612 also plots percentage of estimated critical velocity of a user (y-axis) for two different run types, and using a second methodology for calculation of critical velocity. As such, a user's pace over and endurance/long run (1614) may be equal to approximately 84.5% of the user's critical velocity, and the user's pace over a tempo run (1616) may be equal to approximately 100.2% of the user's critical velocity.

Graph 1618 plots percentage of estimated critical velocity of a user (y-axis) for two different run types, and using a third methodology for calculation of critical velocity. Accordingly, a user's pace over and endurance/long run (1620) may be equal to approximately 81.2% of the user's critical velocity, and the user's pace over a tempo run (1622) may be equal to approximately 96.6% of the user's critical velocity.

In one example, the systems and methods described herein for calculation of an adaptive athletic prescription (which may include a running and/or training prescription) may utilize static or dynamic recommendations. In certain implementations, utilizing a dynamic recommendation may be more personalized, based on individual preferences and data available about the user. In one example, a dynamic recommendation may allow for workouts or any sequence of athletic activity to be chosen and completed more frequently, and/or may be implemented such that users will enjoy them more because they are a better individual fit for that user.

In one example, data used to calculate dynamic recommendations for a user may include one or more of the following information sources: user metadata, user preferences, workout metadata, workout completion data, user interaction data related to user interaction with an activity monitoring device, and combinations thereof, amongst others. In one implementation, machine learning techniques may be utilized using this data to derive the intelligence behind workout recommendations. In one specific example, a collaborative filtering apparatus may be utilized. The apparatus may include a processor and a computer-readable medium comprising computer-executable instructions that when executed by the processor are configured to perform collaborative filtering processes. In one embodiment, the collaborative filtering apparatus is a component of another device, such as one or more of the devices disclosed herein. The collaborative filtering may utilize existing workout completion data to predictively determine how likely users are to complete workouts they haven't completed and/or had an opportunity to complete prior to the instance of determination.

In certain examples, the machine learning methodology described herein, as well as the neural network methodology described later, may be utilized to generate an adaptive athletic activity prescription and/or to adapt the prescription based on one or more athletic performances (e.g. both machine learning and neural network methodology may be utilized at blocks 610 and 612 of flowchart 600).

In accordance with aspects of this disclosure, machine learning methodology may, in certain examples, utilize a number of variable parameters in one or more calculations in identifying a model with a best predictive ability for workout recommendations. These parameters may include, but are not limited to, the following examples and/or the non-limiting embodiments provided below:

A) Data type: In certain implementations, this parameter may relate to the data that gets inputted into the model. In one example, this parameter may relate to workout completion events such that every time a user completes a workout, related data gets inputted into the model as a data point.

B) Amount of data: In certain implementations, this parameter may relate to an aggregate quantity of data is obtained (which may be via multiple sources) and inputted into the model. In one example, this parameter may represent how many days (or weeks) worth of workout completion data to input into the model. In some embodiments, sampling rate may be considered.

C) Data divisions: In certain embodiments, this parameter may relate to a portion (e.g., such as a percentage) of the workout completion data that goes toward the training set, cross-validation set, and/or test set, and/or determinations relating to how individual workout completion events are assigned to each set.

D) Accuracy metric: In certain embodiments, this parameter may relate to how different versions of the trained collaborative filtering models are evaluated against each other. This parameter may be used to judge which collaborative filtering model generates the "best" workout recommendations, which may be determined with one or more standards.

E) Model type: In certain embodiments, an alternating least squares ("ALS") package may include multiple versions of collaborative filtering, such as "explicit" and "implicit" models. This choice represents two inherently different ways of interpreting and processing the available data. In one example, an implicit model may be used in the described non-limiting examples that follow.

i) Rank: In certain embodiments, this parameter may relate to a quantity of features to use for the model.

ii) Iterations: In certain embodiments, this parameter may relate to a number of iterations of the alternating least squares (ALS) algorithm to run through.

iii) Lambda: In certain embodiments, this may be utilized as regularization parameter that controls overfitting of the model.

iv) Alpha: In certain embodiments, this may be utilized as a confidence parameter that controls how much weight is given to positive examples in the training set. For example, in one embodiment, it may be used to determine how much confidence is there that a user (or group) completing a workout means they liked that workout, or would do that workout (or a similar workout) again. For example, the higher the alpha, the higher this confidence level may be.

In accordance with certain systems and methods, determining a best collaborative filtering model for workout recommendations may include deciding how much data to collect, input, and/or utilize in one or more calculations. In one example, 8 weeks (approximately 2 months) of data may be used to train the model in. However, it is contemplated that any duration may be utilized, without departing from the scope of these disclosures. The data frequency, sampling rate, accuracy and/or other factors may influence duration in some embodiments. Subsequently, the data may be split up into a training set, cross-validation set, and/a test set. In one example, this splitting may be done randomly to ensure that no bias gets introduced by the way the data is split up. However, in other instances, a different division of data may be utilized.

In one implementation, a real production workout recommender may be executed at a fixed point of time, and utilizing workout completion data it has received/stored up to a specific point in time, including but not limited to, the time of execution. The real production workout recommender may create workout recommendations, with the intent that sometime in the future a user will complete the recommended workouts. To more closely match this real-world use case, data may be split up temporally. A model may be created using data before a certain point in time, and the accuracy of that model may be evaluated based on data after that point in time.

In one example, a first time period of workout completion event data may be utilized to create a best model, and a second time period may be utilized to evaluate the quality of the recommendations generated by that model. The determinations may be of a duration or percentage of a fixed time. In yet other embodiments, the time periods may be dynamically adjusted. In one embodiment of an 8-week plan, the first time period may be 6 weeks in which workout completion data from this time is utilized to create a best model and the last 2 weeks of the 8-week timeframe may be utilized to evaluate the quality of the recommendations generated by that model. In one implementation, this methodology may mimic a real-world scenario where workout recommendations are generated based on 6 weeks of past data, and workouts are recommended going forward. Similarly, 6 weeks of model creation data may be split into 4 weeks of training data, and 2 weeks of cross-validation data. These are merely examples.

In certain implementations, an accuracy metric may be utilized. For example, given the division of data, different models may be selected from, and the selected model may be evaluated. It may be intended that the model may recommend workouts that a user is likely to complete (and/or determines if of an acceptable range of difficulty, enjoyment, or other quality metric), and it may be decided that the best way to measure the quality of models is by seeing how likely it is that the workouts the model recommend are actually completed by the user in the future (which may be approximated using the cross-validation set and the test set). In one embodiment, the accuracy of the model, for example, as the percentage of workouts, that the recommender recommends that actually get completed in the evaluation set may be determined. However, with this accuracy metric there is the possibility that the model would recommend workouts to a user, but the user won't actually do any workouts (or do very few workouts) in the dataset that we are using to evaluate the model. In this case, even the best recommender system would not work. For example, if the user goes on vacation for 2 weeks and does zero workouts, the model may still be accurate. Similarly, if a user who does the entire library of workouts in the 2 weeks used to evaluate the model, even the worst recommender would work well, since the user completed every single workout. Further, there may be a problem of deciding how many workouts the recommender should recommend.

Certain embodiments may determine be to use a modified version of the accuracy metric defined above. The accuracy metric may be defined as the percentage of completed workouts in the evaluation set that the model recommended for the user. For each user, one may recommend however many workouts they actually completed in the evaluation set. This may solve the problems described above. For example, if user A completed 3 workouts in the last 2 weeks of an 8-week timeframe (the test set), then the model may recommend 3 workouts for that user. As such, the number of recommended workouts that match up with the workouts the user actually did may contribute toward the accuracy metric of that model. If user B completed 1 workout in the last 2 weeks, then 1 workout may be recommended to user B, and one or more processes may be executed to check whether the recommendation matched up with the workout user B actually did.

There are numerous other accuracy metrics that may be used, including:

Execute one or more processes to have the recommender rank all of the workouts for each user. Then, for each actual completed workout, check where the recommender ranked that workout. The lower the rank, the better the model.

Execute one or more processes to have the recommender recommend a fixed number of workouts for each user.

Execute one or more processes to have the recommender exclude workouts the user did during the training set, so that it only recommends new workouts.

Model Parameters

Tuning the specific model parameters (rank, iterations, lambda, alpha) may include trying different combinations of the parameters to find the best fit. In one example, for every combination, a fixed number of iterations may be used=20. However, it is contemplated that any number of iterations may be utilized, without departing from the scope of these disclosures.

In one specific example, a best model trained had a rank of 25, a lambda of 2, an alpha of 10, and an accuracy on the cross-validation set of 26.37%. This model had an accuracy on the test set of 21.58%, but when a new model was retrained using these chosen parameters using all 6 weeks of training data, the accuracy on the test set jumped up to 25.21%. When compared to a simple popularity-based model (that recommends the globally most popular workouts for everyone), and an even simpler model that recommends workouts at random. The popularity model had an accuracy on the test set of 15%, and the random model had an accuracy of 2.2% on the test set. As such, the collaborative filtering method may be able to significantly outperform non-machine-learning-based models.

In certain examples, a neural network methodology may be utilized in addition to, or as an alternative to the collaborative filtering machine learning described above. For example, collaborative filtering may restrict the type of data that can be used as predictors, while a neural network may accept all types of input data to predict a same outcome. For adaptive running/training activity prescriptions, collaborative filtering may only be able to use workouts completed as inputs to the model to predict workouts completed at a later time, while a neural network may use workouts completed, percent completion, additional metadata about the workouts (e.g., drills, intensity, equipment), and profile information as model inputs to also predict workouts completed in a future period. Both methods may predict the likelihood of completing each and every workout in the prediction period ranging from 0 to 1.

Neural Network Model Overview:

The feature inputs (of which there may be ~5,000 input features, although it is contemplated that other numbers of input features may be utilized, without departing from the scope of these disclosures) may include:

Average workout completion percentage and standard deviation and Counts over the past 6 weeks may be aggregated for each training/running workout Activity of the following items: workout drill type (i.e. same drill used across multiple workouts), workout intensity (low, moderate, high), workout focus (strength, endurance, mobility, etc.), workout equipment group (None, Basic, Full), workout level (Beginner, Intermediate, Advanced), RPE, and/or workout duration.

These feature inputs may be used to predict workout completion against a library of ~138 workouts. In one example, both feature inputs and predicted workouts may require at least 10 instances in the dataset to be included. Further, the input period (pre-period) may be 6 weeks prior to predict workouts completed in the following 2 weeks (post-period).

In one example, the model may be a multilayer perceptron model that has a drop-out function and L2 regularization built-in to help avoid overfitting the data. The hidden layers may be rectified linear units (RELUs) with a softmax output layer. The loss function may be crossentropy of the softmax and leveraging a stochastic gradient descent optimization. Accuracy may be measured by the top 3 predictions being inclusive of the actual value. However, other numbers of predictions may be utilized, without departing from the scope of these disclosures.

Neural network tuning may consider various parameters, which may include: a number of hidden layers, dropout rate, number of nodes in the hidden layers, optimization method (stochastic gradient descent, adam, and adagrad), learning rate, and/or L2 regularization parameter (prevent overfitting), among others.

Accuracy may be measured as described above (top 3 predictions include actual) and are conveyed as a number of accurate results per mini-batch of 10K that are iterated over 100 iterations/epochs. In certain examples, the results may not reach minimum cost (as defined by stochastic gradient descent) and may be cut-off early to allow for quicker model iterations. For a final model, it may be allowed to iterate until a cost approaching 0 is reached. In one implementation, all of the parameters may be optimized against a training dataset. When we get something that looks favorable, it may be evaluated against the test data set and further tuned.

Aspects of this disclosure relates to an apparatus, a non-transitory computer-readable medium that has computer-executable instructions, and a method for prescribing a running coaching plan/adaptive running activity prescription to a user. Additionally, this running coaching plan may be adapted based on a progression, or lack thereof, of the user through a prescribed set of athletic activities. Advantageously, this disclosure allows for, using, among others, one or more high speed processor elements (e.g. 202-1, 202-2), a complex set of calculations to be executed to arrive at the running coaching plan, and to adapt the running coaching plan based on activities (e.g. runs) carried out by the user. Further the running coaching plan may be continuously updated such that a user is, in one example, constantly presented with an up to date running coaching plan, that takes into account recent athletic activity. In one example, a running coaching plan may be updated during a run on an athletic monitoring device worn by user, or after a run has been completed.

In certain aspects, an apparatus, a non-transitory computer-readable medium that has computer-executable instructions, and a method are described that include a processor, a user interface, a sensor configured to capture data indicative of motion of a user, and store computer-executable instructions that are executed by the processor, and include communicating using the user interface, a request for the user to complete a benchmark running test. Additionally, the instructions may include receiving, from the sensor, motion data associated with one or more of the benchmark running test and a prior running activity undertaken by the user. Biographic and goal data associated with the user may also be received from the user interface. The user may be classified into a running experience classification, based upon one or more of the received motion data and biographic data. Athletic constants may be assigned to the user based upon the running experience classification. A critical velocity a finite work capacity may be calculated for the user, from the received motion data. An adaptive running activity prescription be calculated for the user, based upon the calculated critical velocity, the finite work capacity, the signed athletic constants, and the goal data. Additionally, the calculated adaptive running activity prescription may be adapted, based upon subsequent motion data received from the sensor.

In accordance with one embodiment, the calculated adaptive running activity prescription for the user may also include calculating a new critical velocity and finite work capacity for the user using the subsequent motion data, and calculating a new adaptive running prescription using the new critical velocity environment work capacity for the user.

In another embodiment, the biographic and goal data associated with the user includes an average number of miles run per week and eight dates that the user is participating in a running event in the future.

In one implementation, the calculating of the critical velocity in the finite work capacity of the user includes using motion data received from a single benchmarking running test.

Further, the single benchmarking running test may prescribe that the user run as far as possible within approximately three minutes.

Additionally, the motion data received from the single benchmarking running test may be used to calculate the critical velocity of the user as: critical velocity=(distance covered during the single benchmarking running test)/((time taken to run distance covered^0.918)*1.8677).

In yet another implementation, motion data received from a single benchmarking running test may be used to calculate a finite work capacity of the user as: finite work capacity=(distance covered during the single benchmarking running test)−(critical velocity*time taken to complete single benchmarking running test).

In another embodiment, the critical velocity in the finite work capacity are calculated using motion data received for a prior running activity undertaken by the user. As such, if the prior running activity is a tempo run: critical velocity=1.0*(average velocity of the user during the tempo run), and if the prior running activity is a long run: critical velocity=1.2*(average velocity of user during the long run).

In yet another embodiment, the motion data that includes a prior running activity undertaken by the user is valid if the prior running activity was undertaken by the user within an eligibility window. Further, the eligibility window may be a period of approximately seven days.

In another implementation, the calculating of the adaptive running activity prescription for the user may also include calculating a relative intensity from the motion data for the prior running activity undertaken by the user. The relative intensity may be equal to: (average velocity of user during prior running activity)/(critical velocity of the user).

Further, calculating the adaptive running activity prescription for the user may also include calculating a training impulse from the received motion data.

The received motion data may also include heart rate data and a rate of perceived exertion for the user.

A training impulse may be calculated as being equal to: (relative intensity)*(critical velocity)*(duration of activity).

In another implementation, the assigning of the athletic constants to the user is based upon the received motion data and biographic and goal data, and the athletic constants may include a fitness gain K1, a fatigue gain K2, a fitness decay T1, and a fatigue decay T2.

In yet another implementation, the calculating of the adaptive running activity prescription for the user includes calculating a micro cycle length of a running plan as: microcycle length=(T1*T2)/(T1-T2)*ln(K2/K1).

In another embodiment, the calculating of the adaptive running activity prescription for the user may include calculating a maximum training impulse for each micro cycle in a running plan, with a first maximum training impulse selected from a store lookup table based upon the received biographic data.

In other aspects, an apparatus, a non-transitory computer-readable medium that has computer-executable instructions, and a method are described that include a processor, a user interface, a sensor configured to capture data indicative of motion of a user, and store computer-executable instructions that are executed by the processor, and include communicating using the user interface, a request for the user to complete a benchmark test. Additionally, the instructions may include receiving, from the sensor, motion data associated with one or more of the benchmark test and a prior activity undertaken by the user. Biographic and goal data associated with the user may also be received from the user interface. The user may be classified into an experience classification, based upon one or more of the received motion data and biographic data. Athletic constants may be assigned to the user based upon the experience classification. An adaptive activity prescription may be calculated for the user, using a collaborative filtering machine learning model or a neural network model. Additionally, the calculated adaptive activity prescription may be adapted, based upon subsequent motion data received from the sensor.

The present disclosure is disclosed above and in the accompanying drawings with reference to a variety of examples. The purpose served by the disclosure, however, is to provide examples of the various features and concepts related to the disclosure, not to limit the scope of the invention. One skilled in the relevant art will recognize that numerous variations and modifications may be made to the examples described above without departing from the scope of the present disclosure.

We claim:

1. An apparatus, comprising:
a processor;
a user interface;
a sensor configured to capture data indicative of motion of a user;
a non-transitory computer-readable medium comprising computer-executable instructions that when executed by the processor are configured to perform at least:
transmitting, using the user interface, a request for the user to complete a benchmark running test, wherein the benchmark running test is a single running test during which the user is instructed to run at a self-chosen intensity, for a self-chosen distance and duration;

receiving motion data from the sensor during the benchmark running test;

classifying, based upon at least one of: the received motion data and biographic data of the user, the user into one of a plurality of running experience classifications, each running experience classification being associated with a plurality of athletic constants;

assigning, based upon the running experience classification, athletic constants to the user;

calculating with the processor, and using the received motion data, a critical velocity and a finite work capacity of the user;

calculating and continuously updating, with the processor, an adaptive running activity prescription for the user, the calculation being based upon the calculated critical velocity and the finite work capacity, the assigned athletic constants, and goal data from the user; and continuously adapting and outputting to the user via the user interface, the calculated adaptive running activity prescription for the user during a current run, based upon subsequent motion data received from the sensor, wherein the adaptive running activity prescription for the user includes a daily training impulse (totalDayTRIMP), calculated using sensor data received from a heart rate sensor of the apparatus, an activity duration (activityDuration), average heart rate (avgHeartRate), resting heart rate (restHeartRate), maximum heart rate (maxHeartRate), and gender-specific constants b, k, as:

totalDayTRIMP=totalDayTRIMP+(activityDuration)* ((avgHeartRate-restHeartRate)/(maxHeartRate-restHeartRate)) * k * $e^{(((avgHeartRate-restHeartRate)/(maxHeartRate-restHeartRate)) * b)}$, wherein the user is provided with two or more running activity options calculated to fulfill the calculated daily training impulse, wherein the two or more running activity options are ranked in order of likelihood that the user will complete the activities, based on received completion data from prior events.

2. The apparatus of claim 1, wherein the continuously adapting and outputting the calculated adaptive running activity prescription for the user further comprises:
calculating a new critical velocity and finite work capacity for the user using the subsequent motion data; and
 calculating a new adaptive running activity prescription using the new critical velocity and finite work capacity for the user.

3. The apparatus of claim 1, wherein the biographic and the goal data associated with the user includes an average number of miles run over a fixed duration of time and a date that the user is participating in a running event in a future.

4. The apparatus of claim 1, wherein the benchmark running test prescribes the user to run as far as possible within three minutes.

5. The apparatus of claim 1, wherein the motion data received from the benchmark running test is used to calculate the critical velocity of the user as: critical velocity=(distance covered during the benchmark running test)/((time taken to run distance covered $^{\wedge}0.918$)*1.8677).

6. The apparatus of claim 5, wherein the motion data received from the benchmark running test is used to calculate the finite work capacity of the user as: finite work capacity=(distance covered during the benchmark running test) −(critical velocity * time taken to complete benchmark running test).

7. The apparatus of claim 1, wherein the calculating of the critical velocity and the finite work capacity of the user comprises using the received motion data obtained during a prior running activity undertaken by the user, wherein the computer-readable medium comprises computer-executable instructions that when executed by the processor perform at least:

determining whether the prior running activity is a tempo run or a long run; and calculating the critical velocity from the determination in which if the prior running activity is a tempo run: critical velocity=1.0 *(average velocity of the user during the tempo run), and wherein if the prior running activity is a long run: critical velocity=1.2 *(average velocity of user during the long run).

8. The apparatus of claim 1, wherein the computer-readable medium further comprises computer-executable instructions that when executed by the processor perform at least:

determining that the received motion data that includes a prior running activity undertaken by the user is valid if the prior running activity was undertaken by the user within an eligibility window.

9. The apparatus of claim 8, wherein the eligibility window is a period of seven days.

10. The apparatus of claim 1, wherein the calculating the adaptive running activity prescription for the user further comprises:

calculating, from the received motion data for a prior running activity undertaken by the user, a relative intensity of the user as: relative intensity=(average velocity of user during prior running activity)/(critical velocity of the user).

11. The apparatus of claim 10, wherein the calculating the adaptive running activity prescription for the user further comprises:

calculating a training impulse from the received motion data.

12. The apparatus of claim 11, wherein the received motion data includes one or more of heart rate data and a rate of perceived exertion of the user.

13. The apparatus of claim 11, wherein the training impulse is calculated as: training impulse=(relative intensity)*(activity duration).

14. The apparatus of claim 1, wherein the assigning the athletic constants to the user is based upon the biographic data and the goal data associated with the user, wherein the athletic constants include a fitness gain (K1), a fatigue gain (K2), a fitness decay (T1), and a fatigue decay (T2).

15. The apparatus of claim 14, wherein the calculating the adaptive running activity prescription for the user further comprises:

calculating a microcycle length of the adaptive running activity prescription as:
microcycle length=(T1*T2)/(T1−T2)*ln(K2/K1).

16. The apparatus of claim 15, wherein the calculating the adaptive running activity prescription for the user further comprises:

calculating a maximum training impulse for each microcycle in the adaptive running activity prescription, wherein a first maximum training impulse is selected from a stored lookup table based on the received biographic data.

17. The apparatus of claim 1, wherein the benchmark running test is not a continuous all-out running test for a predetermined amount of time.

18. The apparatus of claim 1, wherein the benchmark running test includes an instruction to run as far as possible within a predetermined duration.

19. The apparatus of claim 1, wherein the computer-executable instructions, when executed by the processor, are further configured to perform at least:

receiving motion data from prior running activity undertaken by the user.

* * * * *